United States Patent
Musicki et al.

(10) Patent No.: US 10,618,890 B2
(45) Date of Patent: Apr. 14, 2020

(54) BENZIMIDAZOLE SULFONAMIDE DERIVATIVES AS INVERSE AGONISTS OF RETINOID-RELATED ORPHAN RECEPTOR GAMMA (ROR GAMMA (T))

(71) Applicant: GALDERMA RESEARCH & DEVELOPMENT, Biot (FR)

(72) Inventors: Branislav Musicki, Nice (FR); Gilles Ouvry, Biot (FR); Etienne Thoreau, Saint-Vallier-de-Thiey (FR); Claire Bouix-Peter, Vallauris (FR)

(73) Assignee: GALDERMA RESEARCH & DEVELOPMENT, Biot (FR)

( * ) Notice: Subject to any disclaimer, the term of this patent is extended or adjusted under 35 U.S.C. 154(b) by 0 days.

(21) Appl. No.: 15/537,580

(22) PCT Filed: Dec. 18, 2015

(86) PCT No.: PCT/EP2015/080691
§ 371 (c)(1),
(2) Date: Jun. 19, 2017

(87) PCT Pub. No.: WO2016/097393
PCT Pub. Date: Jun. 23, 2016

(65) Prior Publication Data
US 2019/0071433 A1    Mar. 7, 2019

(30) Foreign Application Priority Data

Dec. 19, 2014 (FR) ...................................... 14 63035
Jul. 3, 2015 (FR) ...................................... 15 56341

(51) Int. Cl.
| | | |
|---|---|---|
| C07D 235/26 | (2006.01) | |
| C07D 405/06 | (2006.01) | |
| C07D 405/14 | (2006.01) | |
| C07D 401/06 | (2006.01) | |
| C07D 413/06 | (2006.01) | |
| C07D 215/36 | (2006.01) | |
| C07D 231/56 | (2006.01) | |
| C07D 401/04 | (2006.01) | |
| C07D 403/04 | (2006.01) | |
| C07D 403/06 | (2006.01) | |
| C07D 405/04 | (2006.01) | |
| C07D 405/12 | (2006.01) | |
| C07D 407/04 | (2006.01) | |
| C07D 409/04 | (2006.01) | |
| C07D 409/06 | (2006.01) | |
| C07D 417/06 | (2006.01) | |
| C07D 471/10 | (2006.01) | |
| C07D 209/34 | (2006.01) | |
| C07D 307/79 | (2006.01) | |
| A61P 17/10 | (2006.01) | |
| A61P 17/06 | (2006.01) | |
| A61P 17/04 | (2006.01) | |
| C07D 401/14 | (2006.01) | |

(52) U.S. Cl.
CPC ............ *C07D 413/06* (2013.01); *A61P 17/04* (2018.01); *A61P 17/06* (2018.01); *A61P 17/10* (2018.01); *C07D 209/34* (2013.01); *C07D 215/36* (2013.01); *C07D 231/56* (2013.01); *C07D 235/26* (2013.01); *C07D 307/79* (2013.01); *C07D 401/04* (2013.01); *C07D 401/06* (2013.01); *C07D 401/14* (2013.01); *C07D 403/04* (2013.01); *C07D 403/06* (2013.01); *C07D 405/04* (2013.01); *C07D 405/06* (2013.01); *C07D 405/12* (2013.01); *C07D 405/14* (2013.01); *C07D 407/04* (2013.01); *C07D 409/04* (2013.01); *C07D 409/06* (2013.01); *C07D 417/06* (2013.01); *C07D 471/10* (2013.01)

(58) Field of Classification Search
CPC .. C07D 235/26; C07D 405/06; C07D 405/14; C07D 401/06; C07D 413/06
See application file for complete search history.

(56) References Cited

U.S. PATENT DOCUMENTS

2008/0004288 A1    1/2008   Santhakumar et al.

FOREIGN PATENT DOCUMENTS

| WO | WO-2006/052190 A1 | 5/2006 |
| WO | WO-2011/137089 A1 | 11/2011 |
| WO | 2013/160418 A1 | 10/2013 |
| WO | 2014/090712 A1 | 6/2014 |

OTHER PUBLICATIONS

Chemical Abstracts Registry No. 914244-66-9, indexed in the Registry file on STN CAS Online on Nov. 29, 2006. (Year: 2006).*
Chemical Abstracts Registry No. 924168-33-2, indexed in the Registry file on STN CAS Online on Mar. 1, 2007. (Year: 2007).*
Chemical Abstracts Registry No. 950052-33-2 {indexed in the Registry file on STN CAS Online on Oct. 10, 2007. (Year: 2007).*
Chemical Abstracts Registry No. 1328091-23-1 {indexed in the Registry file on STN CAS Online on Sep. 4, 2011. (Year: 2011).*
Chemical Abstracts Registry No. 1387015-28-2, indexed in the Registry file on STN CAS Online on Aug. 6, 2012. (Year: 2012).*

(Continued)

*Primary Examiner* — Laura L Stockton
(74) *Attorney, Agent, or Firm* — Sunit Talapatra; Foley & Larder LLP

(57) ABSTRACT

Benzimidazole sulfonamide derivatives of formula (I), the pharmaceutically acceptable addition salts thereof, the hydrates and/or solvates thereof, and the use of same as inverse agonists of retinoid-related orphan receptor gamma RORγt are described.
Pharmaceutical compositions including such compounds, as well as the use thereof for the topical and/or oral treatment of RORγt receptor-mediated inflammatory diseases, in particular acne, psoriasis and/or atopic dermatitis are also described.

13 Claims, No Drawings

(56) References Cited

OTHER PUBLICATIONS

International Search Report dated Mar. 7, 2016 corresponding to International Patent Application No. PCT/EP2015/080691 (with English translation), 6 pages.
Zhang, Y., et al., "Discovery of 2-oxo-1,2-dihydrobenzo[cd]indole-6-sulfonamide derivatives as new RORγ inhibitors using virtual screening, synthesis and biological evaluation," European J. Med. Chem., vol. 78, Mar. 2014, pp. 431-444, XP028847891.

* cited by examiner

BENZIMIDAZOLE SULFONAMIDE DERIVATIVES AS INVERSE AGONISTS OF RETINOID-RELATED ORPHAN RECEPTOR GAMMA (ROR GAMMA (T))

CROSS-REFERENCE TO RELATED APPLICATIONS

This application is the National Phase of International Patent Application No. PCT/EP2015/080691, filed Dec. 18, 2015, published on Jun. 23, 2016 as WO 2016/097393 A1, which claims priority to French Application No. 1556341, filed Jul. 3, 2015. The contents of these applications are herein incorporated by reference in their entirety.

The present invention relates to particular bicyclic sulfonamide derivatives, to the pharmaceutically acceptable addition salts thereof, hydrates thereof and/or solvates thereof, and also to the use thereof as inverse agonist of the retinoid-related orphan receptor gamma RORγt.

The invention also relates to a pharmaceutical composition comprising such compounds and also to the use thereof for the topical and/or oral treatment of inflammatory diseases mediated by the RORγt receptors, especially acne, atopic dermatitis and/or psoriasis.

The nuclear receptors form a large family (known as a superfamily) of transcription factors which correspond to proteins that are capable of being activated by a ligand, of binding to specific DNA sequences and of regulating the transcription of target genes. Thus, these receptors are involved in the regulation of a wide variety of biological functions, including growth, development, reproduction, differentiation and metabolism in a multitude of living organisms.

The first members of this superfamily that were identified and described in the scientific literature are the nuclear receptors of steroid hormones such as the glucocorticoid receptors and the estrogen receptors. This superfamily also comprises among its members many receptors for which no ligand has been identified. These nuclear receptors are known as "orphan receptors".

Retinoid-related orphan receptors thus constitute a subfamily of nuclear receptors. This subfamily is composed of three members each having an intrinsic expression profile: ROR alpha (known as RORα), ROR beta (known as RORβ) and ROR gamma (known as RORγ). Two isoforms of the orphan receptors RORγ have already been identified, namely RORγ1, which is expressed in a variety of tissues such as the thymus, the kidneys, muscles and the liver, and RORγ2 (also known as RORγt), which is expressed exclusively in the cells of the immune system.

In particular, the receptor RORγt plays an important regulating role in cell differentiation of the Th17 lymphocytes which correspond to helper T lymphocytes whose function is to ensure the defence of the body against a large number of extracellular pathogens such as bacteria and fungal infections.

However, it has been demonstrated that the Th17 lymphocytes are also involved in a wide variety of inflammatory disorders, such as acne, and of autoimmune diseases such as psoriasis, rheumatoid arthritis or multiple sclerosis (Peck A, Mellins E D. Precarious balance; Th17 cells in host defense. Infect. Immun. 2010 January; 78(1): 32-8; Suarez-Farinas: J. Allergy Clin. Immunol. 2014; J. Invest. Dermatol. 2008, 128(11), 2625).

Specifically, the Th17 lymphocytes produce numerous cytokines which have distinct profiles, such as interleukin-17A (IL-17A), interleukin-17F (IL-17F), interleukin-26 (IL-26), interleukin-21 (IL-21), interleukin-22 (IL-22) and TNFα, the development, survival and proliferation of which depend on interleukin-23 (IL-23). These cytokines are capable of activating different types of effector cells, such as keratinocytes, thus leading to their hyperproliferation and to the additional production of pro-inflammatory cytokines, chemokines and antimicrobial peptides, which in turn recruit and activate other immune system cells in the inflamed skin, which may lead to amplification of the inflammatory response.

Thus, activation of the Th17 lymphocytes is responsible for the recruitment of cytokines, especially of interleukin-17 (IL17), and of other types of pro-inflammatory cells, which will lead to the mediation of inflammatory disorders such as acne and/or of autoimmune diseases such as psoriasis.

Experiments conducted on mice show that a decrease in the level of expression of the RORγt receptor leads to a decrease in the activity of the Th17 lymphocytes, which consequently makes it possible to greatly reduce the expression of interleukin-17 (IL-17) (Ivanov II, McKenzie B S, Zhou L, Tadokoro C E, Lepelley A, Lafaille J J, Cua D J, Littman D R: Cell 2006, 126, 1121-1133) and to efficiently treat inflammatory disorders and autoimmune diseases mediated by these cytokines, especially those for which high levels of interleukin-17 (IL-17) are detected.

To this end, patent application WO 2013/160 418 describes sulfonamide compounds used as inverse agonists of the RORγt receptor in order to be able to treat inflammatory disorders and autoimmune diseases. Similarly, other compounds have also been developed as inverse agonists of the RORγt receptor, such as those described in patent applications WO 2014/090 712, WO 2014/008 214, WO 2013/169 588, WO 2013/160 419, WO 2013/1 002 027, WO 2013/092 939, WO 2013/092 941, WO 2013/085 890 and WO 2012/100 732.

There is thus a real need to develop novel compounds as inverse agonists of the RORγt receptor in order to be able to efficiently treat diseases mediated by such a receptor, especially inflammatory disorders such as acne, and/or autoimmune diseases such as psoriasis or atopic dermatitis.

This aim is achieved by means of the use of particular bicyclic sulfonamide derivatives as described below, which make it possible to modulate the activity of the RORγt receptor and consequently to efficiently treat inflammatory disorders and autoimmune diseases of certain pathologies.

One subject of the present invention is thus in particular one or more compounds of formula (I), the pharmaceutically acceptable addition salts thereof, hydrates thereof and/or solvates thereof:

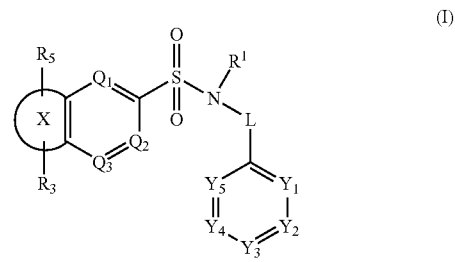

in which formula (I):
L represents a single bond or a methylene group $CH_2$,
X represents the following cyclic radical:

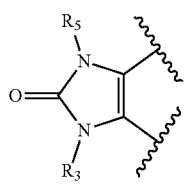

one or two of the elements $Y^1$, $Y^2$, $Y^3$, $Y^4$ and $Y^5$ represent(s) a nitrogen atom and the other elements correspond to a group —$CR^2$, or each of the elements $Y^1$, $Y^2$, $Y^3$, $Y^4$ and $Y^5$ corresponds to a group —$CR^2$, one or two of the elements $Q^1$, $Q^2$ and $Q^3$ represent(s) a nitrogen atom and the other element(s) correspond(s) to a group —$CR^{2a}$, or each of the elements $Q^1$, $Q^2$ and $Q^3$ corresponds to a group —$CR^{2a}$, $R^1$ represents a linear or branched $C_3$-$C_5$ alkyl radical, a $C_3$-$C_5$ cycloalkyl radical, a linear or branched $C_2$-$C_5$ alkenyl radical, a $(C_1)$alkyl$(C_3$-$C_5)$cycloalkyl radical, a $C_4$-$C_5$ heterocycloalkyl radical, a $(C_1)$alkyl$(C_4$-$C_6)$heterocycloalkyl radical, $R^2$ represents a hydrogen atom or a halogen atom, a linear or branched $C_1$-$C_5$ alkyl radical, a linear or branched $C_2$-$C_4$ alkenyl radical, a $C_1$-$C_4$ alkoxy radical, a cyano group —CN, a radical —C(=O)$R'^2$ with $R'^2$ denoting a $C_1$-$C_3$ alkoxy radical, a —$CF_3$ radical; said alkyl, alkenyl and alkoxy radicals possibly being substituted with one or more halogen atoms;

$R^{2a}$ represents a hydrogen atom or a halogen atom, a linear or branched $C_1$-$C_5$ alkyl radical, a linear or branched $C_2$-$C_4$ alkenyl radical, a $C_1$-$C_4$ alkoxy radical, a —CN group, a hydroxyl group —OH, a group —CH($R^{3a}$)OH, a carboxylic group —COOH, a carbamoyl group —CONR$^{2c}$R$^{2d}$, an amido group —NR$^{2c}$COR$^{2d}$, a group —SO$_2$R$^{2c}$, a group —SOR$^{2c}$, a group —S(=O)(=NH—R$^{2C}$), said alkyl, alkenyl and alkoxy radicals possibly being substituted with one or more halogen atoms, $R^{2c}$ and $R^{2d}$, which may be identical or different, represent a hydrogen atom or a linear or branched $C_1$-$C_5$ alkyl radical;

$R^{3a}$ represents a hydrogen atom or a linear or branched $C_1$-$C_5$ alkyl radical;

$R^3$ represents a hydrogen atom or a group (CHR$^6$)$_n$—(Z)$_o$—(CHR$'^6$)$_p$—R$^7$, a group CH=R$^7$ or a group —C=CH—R$^7$, n, o and p, which may be identical or different, represent zero or a natural integer ranging from 1 to 3, Z represents a divalent group chosen from a methylene group —CH$_2$—, an amino group —NH— and an oxygen atom —O—, $R^6$ and $R'^6$, which may be identical or different, represent a hydrogen atom, a methyl group —CH$_3$, a group —OH, a $C_1$ hydroxyalkyl group, a carboxylic function —COOH, $R^7$ represents:

a hydrogen atom or a halogen atom, a group COOR$'^7$ with R$'^7$ denoting (C$_1$)alkyl(C$_6$)heterocycle, a non-cationic heterocyclic radical optionally substituted with one or more halogen atoms, one or more linear or branched $C_1$-$C_3$ alkyl groups, one or more —OH groups, one or more carbonyl functions, one or more linear or branched $C_1$-$C_4$ hydroxyalkyl groups, one or more amino groups, one or more groups C(=O)R$_{7a}$; one or more groups S(=O)$_2$R$_{7a}$; R$_{7a}$ representing a linear or branched $C_1$-$C_3$ alkyl radical, a linear or branched $C_1$-$C_3$ alkoxy radical, or an amino radical N(R$^{8a}$)(R$^{8b}$), a non-cationic $C_3$-$C_6$ cycloalkyl radical optionally substituted with one or more $C_1$ alkyl radicals, one or more halogen atoms, a cyano group —CN or one or more groups —COR$^9$; R$^9$ denoting a linear or branched $C_1$-$C_3$ alkoxy radical, or a hydroxyl group, an aromatic or heteroaromatic, non-cationic radical optionally substituted with one or more halogen atoms, one or more linear or branched $C_1$-$C_3$ alkyl groups optionally substituted with one or more halogen atoms, one or more $C_1$-$C_3$ alkoxy groups, one or more amino groups —NR$^{11}$R$^{12}$, one or more groups —COR$^{11}$, one or more groups —COOR$^{11}$, one or more amido groups —CONR$^{11}$R$^{12}$, one or more groups —SOR$^{11}$, one or more groups —SO$_2$R$^{11}$, one or more groups —NH-COR$^{11}$, one or more groups —NHCOOR$^{11}$, one or more groups —SO$_2$NR$^{11}$R$^{12}$ or one or more —CN groups; R$^{11}$ and R$^{12}$, which may be identical or different, representing a hydrogen atom, a hydroxyl radical —OH, a linear or branched $C_1$-$C_3$ alkyl radical optionally substituted with one or more halogen atoms, when $R^3$ represents a group —CH=R$^7$ or a group —C=CH—R$^7$, then R$^7$ does not represent a hydrogen atom, a halogen atom or a group COOR$'^7$, $R^5$ represents a hydrogen atom or a halogen atom, a linear or branched $C_1$-$C_3$ alkyl radical optionally substituted with one or more halogen atoms; an amino radical —NH$_2$, a radical CH$_2$R$'^{7a}$ with R$'^{7a}$ denoting a $C_1$ alkoxy radical, a hydroxyl group —OH, a —CH$_2$COOH group, a group —CH(R$^{5b}$)OH, an amino group —NH$_2$, a carboxylic group —COOH, a —CN group, a thioxo function, $R^{5b}$ represents a hydrogen atom; a linear or branched $C_1$-$C_3$ alkyl radical optionally substituted with one or more carboxylic functions; a cyclopropyl radical, $R^{8a}$ and $R^{8b}$, which may be identical or different, denote a hydrogen atom, a linear or branched $C_1$-$C_3$ alkyl radical or a cyclopropyl radical.

The compound(s) according to the invention thus correspond to bicyclic sulfonamide derivatives, and thus to one or more sulfonamide compounds bearing in their structure at least two rings that are fused to each other.

In accordance with the definition of formula (I), the endocyclic bond between the cyclic radical X, as represented above, and the aromatic nucleus comprising the elements $Q_1$ to $Q_3$ is a double bond. Thus, the double bond is common between the cyclic radical X and the aromatic nucleus comprising the elements $Q_1$ to $Q_3$. The endocyclic double bond can delocalize within the aromatic nucleus comprising the elements $Q_1$ to $Q_3$.

The compounds according to the invention make it possible to modulate, i.e. to inhibit, the activity of the RORγt receptor.

A subject of the present invention is also the compound(s) as defined previously, as medicament and cosmetic.

Another subject of the invention relates to the compound(s) as defined previously for their use in the treatment of diseases mediated by the RORγt receptor, especially inflammatory disorders and/or autoimmune diseases mediated by the RORγt receptor.

Moreover, the invention also relates to a pharmaceutical composition comprising, in a pharmaceutically acceptable medium, one or more compounds of formula (Ia) as defined previously, pharmaceutically acceptable addition salts thereof, hydrates thereof and/or solvates thereof.

The present invention also relates to the pharmaceutical composition as described previously, for its use in the treatment of diseases mediated by the RORγt receptor, especially inflammatory disorders and/or autoimmune diseases.

Finally, the invention relates to a method for treating diseases mediated by the RORγt receptor, comprising the administration, especially topically or orally, of a therapeutically effective amount of one or more compounds as defined above to a patient.

Other subjects, characteristics, aspects and advantages of the invention will emerge even more clearly on reading the description and the examples that follow.

According to one embodiment, in formula (I), L represents a single bond.

According to another embodiment, in formula (I), L represents a methylene group —$CH_2$.

Preferentially, in formula (I), L represents a single bond.

Preferentially, $R^3$ is other than a halogen atom and $R^5$ represents a hydrogen atom or a linear or branched $C_1$-$C_3$ alkyl radical optionally substituted with one or more halogen atoms.

According to one embodiment, $R^3$ represents a hydrogen atom, a group $(CHR^6)_n$—$(Z)_o$—$(CHR'^6)_p$—$R^7$ and $R^5$ represents a hydrogen atom or a linear or branched $C_1$-$C_3$ alkyl radical, optionally substituted with one or more halogen atoms.

According to one embodiment, in formula (I), $R^3$ represents a hydrogen atom.

According to one embodiment, in formula (I), $R^3$ represents a group $(CHR^6)_n$—$(Z)_o$—$(CHR'^6)_p$—$R^7$.

According to one embodiment, in formula (I), the indices n, o and p, which may be identical or different, denote zero.

According to one embodiment, in formula (I), the indices n, o and p, which may be identical or different, denote a natural integer ranging from 1 to 3.

According to one embodiment, in formula (I), the indices n and p denote zero and the index o is equal to 1.

According to one embodiment, in formula (I), Z represents a methylene group —$CH_2$.

According to one embodiment, in formula (I), Z represents a divalent group —O—.

According to one embodiment, in formula (I), Z represents a divalent group —NH—.

According to one embodiment, in formula (I), $R^3$ represents a group Z—$R^7$, with Z having the meaning described previously.

According to a particular embodiment, in formula (I), $R^3$ represents a group —$CH_2$—$R^7$.

According to a particular embodiment, in formula (I), $R^3$ represents a group —O—$R^7$.

According to a particular embodiment, in formula (I), $R^3$ represents a group —NH—$R^7$.

According to one embodiment, in formula (I), $R^7$ represents a heterocyclic radical chosen from the following heterocycles:

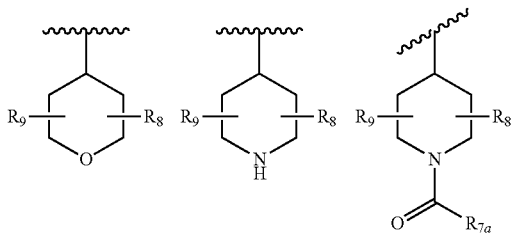

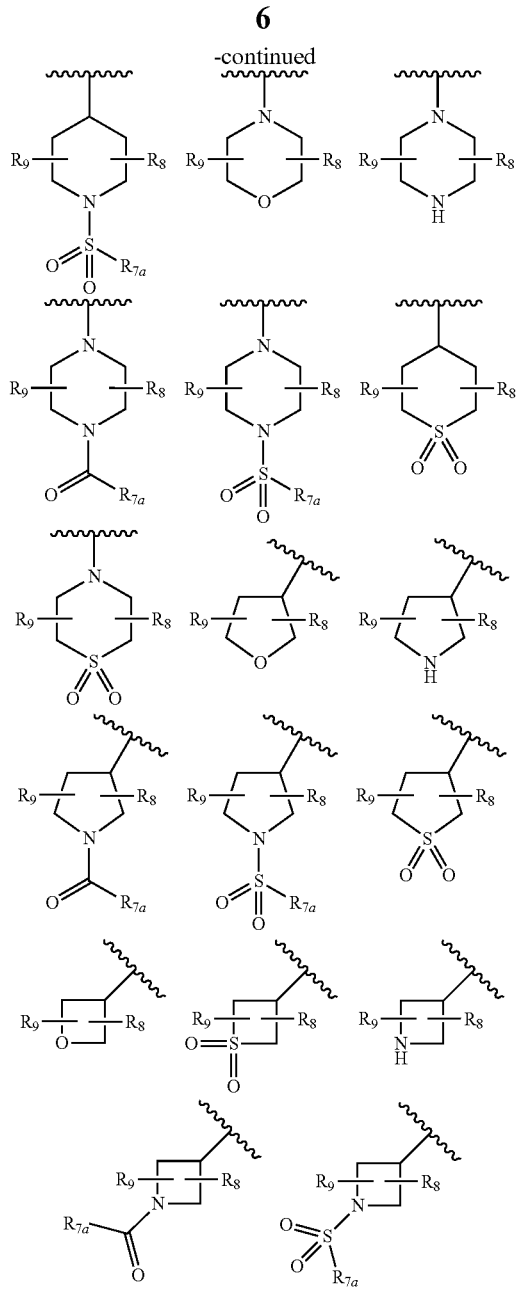

in which:

$R_{7a}$ represents a linear or branched $C_1$-$C_3$ alkyl radical, a linear or branched $C_1$-$C_3$ alkoxy radical or an amino radical $N(R^{8a})(R^{8b})$, $R^{8a}$ and $R^{8b}$, which may be identical or different, denote a hydrogen atom, a linear or branched $C_1$-$C_3$ alkyl radical or a cyclopropyl radical, $R_8$ and $R_9$, which may be identical or different, represent a hydrogen atom, a linear or branched $C_1$-$C_3$ alkyl radical, a hydroxyl group —OH, a carbonyl function =O, a ($C_1$)hydroxyalkyl radical (—$CH_2OH$), an amino group $NH_2$, $R_8$ and $R_9$ can form, together with the carbon atoms to which they are attached, a 5- to 7-membered carbocyclic ring.

According to one embodiment, in formula (I), $R^7$ represents an aromatic or heteroaromatic radical chosen from:

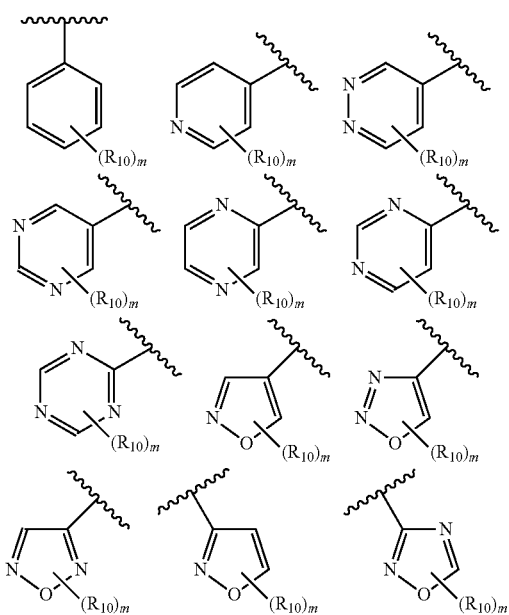

in which:
R$_{10}$ represents a hydrogen atom or a halogen atom, a linear or branched C$_1$-C$_3$ alkyl group optionally substituted with one or more halogen atoms, a C$_1$-C$_3$ alkoxy group, an amino group —NR$^{11}$R$^{12}$, a group —COR$^{11}$, a group —COOR$^{11}$, an amido group —CONR$^{11}$R$^{12}$, a group —SOR$^{11}$, a group —SO$_2$R$^{11}$, a group —NHCOR$^{11}$, a group —NHCOOR$^{11}$, a group —SO$_2$NR$^{11}$R$^{12}$ or a —CN group; R$^{11}$ and R$^{12}$, which may be identical or different, representing a hydrogen atom or a linear or branched C$_1$-C$_3$ alkyl radical optionally substituted with one or more halogen atoms,
m denotes zero or a natural integer ranging from 1 to 3.

Preferentially, R$^7$ represents an aromatic or heteroaromatic radical as defined previously, optionally substituted with one or more methyl groups —CH$_3$, one or more methoxy groups —OCH$_3$, one or more hydroxyl groups —OH, one or more amino groups —NH$_2$, one or more —CH$_2$OH groups, one or more cyano groups —CN, one or more halogen atoms or one or more carbonyl functions.

According to one embodiment, the index m is equal to zero.

According to one embodiment, the index m denotes a natural integer ranging from 1 to 3.

Preferentially, the index m is equal to 1.

According to one embodiment, in formula (I), each of the elements Y$^1$, Y$^2$, Y$^3$, Y$^4$ and Y$^5$ corresponds to a group —CR$^2$ with R$^2$ having the same meaning as that described previously.

According to one embodiment, in formula (I), each of the elements Y$^1$, Y$^2$, Y$^3$, Y$^4$ and Y$^5$ corresponds to a group —CR$^2$ with R$^2$ representing a hydrogen atom.

According to one embodiment, in formula (I), each of the elements Y$^1$, Y$^2$, Y$^3$, Y$^4$ and Y$^5$ corresponds to a group —CR$^2$ with R$^2$ representing a linear or branched C$_1$-C$_5$ alkyl radical.

According to one embodiment, in formula (I), each of the elements Q$^1$, Q$^2$ and Q$^3$ represents a group —CR$^{2a}$ with R$^{2a}$ having the same meaning as that described previously.

According to one embodiment, in formula (I), each of the elements Q$^1$, Q$^2$ and Q$^3$ represents a group —CR$^{2a}$ with R$^{2a}$ representing a hydrogen atom.

According to one embodiment, in formula (I), Q$^1$ and Q$^2$ represent a group —CR$^{2a}$ with R$^{2a}$ representing a hydrogen atom and Q$^3$ represents a group —CR$^{2a}$ with R$^{2a}$ representing a linear or branched C$_1$-C$_5$ alkyl radical.

According to one embodiment, in formula (I), R$^1$ represents a linear or branched C$_3$-C$_5$ alkyl radical, preferably a branched C$_3$-C$_5$ and more preferentially branched C$_4$ alkyl radical.

According to one embodiment, in formula (I), R$^1$ represents a C$_3$-C$_5$ cycloalkyl radical, preferably cyclopropyl.

According to one embodiment, in formula (I), R$^1$ represents a linear or branched C$_2$-C$_5$ alkenyl radical.

According to one embodiment, in formula (I), R$^1$ represents a CH$_2$—(C$_3$-C$_5$)cycloalkyl radical.

According to one embodiment, in formula (I), R$^1$ represents a C$_4$-C$_5$ heterocycloalkyl radical.

According to one embodiment, in formula (I), R$^1$ represents a CH$_2$—(C$_4$-C$_6$)heterocycloalkyl radical, in particular a CH$_2$—(C$_4$-C$_5$)heterocycloalkyl radical.

Preferentially, R$^1$ represents a linear or branched C$_3$-C$_5$ alkyl radical, or a CH$_2$—(C$_4$-C$_5$)heterocycloalkyl radical.

According to one embodiment, R$^5$ represents a hydrogen atom.

Preferably, the compound(s) of formula (I) are chosen from the compound(s) of formula (IV), the pharmaceutically acceptable addition salts thereof, hydrates thereof and/or solvates thereof:

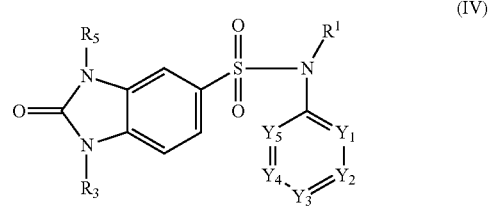

(IV)

in which formula (IV) R$^1$, R$^3$, R$^5$ and Y$^1$ to Y$^5$ have the same meanings as in formula (I) described previously.

Preferentially, R$^1$ represents a linear or branched C$_3$-C$_5$ alkyl radical, or a C$_3$-C$_5$ cycloalkyl radical. More preferentially, R$^1$ represents a linear or branched, especially branched, C$_3$-C$_5$ alkyl radical.

Preferably, Y$^1$-Y$^2$ and Y$^4$-Y$^5$ correspond to a group —CR$^2$ with R$^2$ denoting a hydrogen atom and Y$^3$ corresponds to a group —CR$^2$ with R$^2$ denoting a linear or branched C$_1$-C$_5$ and preferably C$_2$ alkyl radical.

Preferably, Y$^1$ and Y$^3$ are identical and correspond to a group —CR$^2$ with R$^2$ denoting a hydrogen atom or a linear or branched C$_1$-C$_5$ and preferably C$_2$ alkyl radical.

Preferentially, Y$^1$ and Y$^3$ are identical and correspond to a group —CR$^2$ with R$^2$ denoting a hydrogen atom or a linear or branched C$_1$-C$_5$ and preferably C$_2$ alkyl radical.

Preferably, R$^5$ represents a hydrogen atom.

Preferably, R$^3$ represents a group (CHR$^6$)$_n$—(Z)$_o$—(CHR$'^6$)$_p$—R$^7$ with the indices n, p, o, R$^6$, R$'^6$ and R$^7$ having the meanings indicated previously, and preferably R$^7$ is chosen from the heterocyclic radicals and the aromatic or heteroaromatic radicals described previously.

More preferentially, R$^3$ represents a group CH$_2$—R$^7$.

According to one embodiment, R$^1$ represents a linear or branched C$_3$-C$_5$ alkyl radical, R$^5$ represents a hydrogen atom and R$^3$ represents a group (CHR$^6$)$_n$—(Z)$_o$—(CHR$'^6$)—R$^7$ with the indices n, p, o, R$^6$, R$'^6$ and R$^7$ having the meanings indicated previously.

The compounds of formula (I) may be in the form of pharmaceutically acceptable salts. Examples of pharmaceutically acceptable salts are described in Berge et al., 1977, "Sels pharmaceutiquement acceptables" [Pharmaceutically acceptable salts], J. Pharm. Sci., Vol. 66, pages 1-19.

In particular, when the compounds of formula according to the invention are in the form of salts, then the electrical neutrality of said compounds is ensured by an external cationic counterion Y which may be organic or mineral.

Y may be chosen from suitable inorganic cations such as alkali metal ions, especially $Na^+$, $K^+$, alkaline-earth metal ions, especially $Ca^{2+}$, $Mg^{2+}$, or alternatively other cations such as the aluminum ion $Al^{3+}$.

Y may be chosen from suitable organic cations such as the ammonium ion $NH_4^+$, substituted ammonium ions such as $NH_3R^+$, $NHR_2^+$, $NR_4^+$ with R representing a $C_1$-$C_4$ alkyl radical.

In particular, the substituted ammonium ions are those chosen from derivatives of ethylamine, diethylamine, dicyclohexylamine, triethylamine, butylamine, ethylenediamine, ethanolamine, diethanolamine, piperazine, benzylamine, phenylbenzylamine, choline, melglumine and tromethamine, and amino acids such as lysine and arginine.

An example of a quaternary ammonium ion may be the ion $N^+(CH_3)_4$.

The compound(s) according to the invention may be in the form of the solvates thereof.

For the purposes of the present invention, the term "solvate" means a complex of solute (i.e. the compound according to the invention or the salt of said compound) and of solvent.

If the solvent is water, then the solvate may suitably be considered as a hydrate, for example, a hemihydrate, a monohydrate, a dihydrate, a trihydrate, etc.

For example, the solvates and/or hydrates may be obtained directly at the end of the synthetic process, the target compound being isolated in the form of a hydrate, for example a monohydrate or hemihydrate, or in the form of a solvate of the reaction and/or purification solvent.

Unless otherwise indicated, any reference to a compound according to the invention also includes the solvate or the hydrate of the corresponding compound.

Typical processes for the preparation and identification of hydrates and solvates are well known to those skilled in the art: see, for example, pages 202-209 of KJ Guillory, "Generation of Polymorphs, Hydrates, Solvates, and Amorphous Solids" in Polymorphism in Pharmaceutical Solids, edition. Harry G. Britain, Vol. 95, Marcel Dekker, Inc., New York, 1999.

The hydrates and solvates may be isolated and characterized via methods known in the art, such as thermogravimetric analysis (TGA), TGA-mass spectroscopy, TGA-infrared spectroscopy, x-ray powder diffraction, Karl Fischer titration, high-resolution x-ray diffraction, and the like.

Preferably, the compound(s) of formula (I) are chosen from the compounds as described in the tables below, and also the pharmaceutically acceptable addition salts thereof, hydrates thereof and/or solvates thereof:

TABLE 1

| | | IC50 hRORg | IC50 hCD4/IL17 |
|---|---|---|---|
| 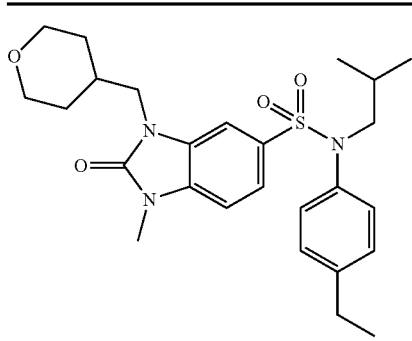 | 1-methyl-2-oxo-3-(tetrahydropyran-4-ylmethyl)-2,3-dihydro-1H-benzimidazole-5-sulfonic acid (4-ethylphenyl)isobutylamide Compound 1 | C | ND |
| 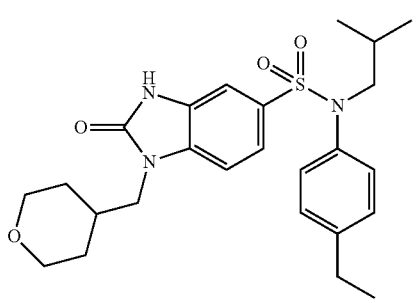 [SMILES: CCc1ccc(N(CC(C)C)S(=O)(=O)c2ccc3c(c2)[nH]c(=O)n3CC2CCOCC2)cc1] | 2-oxo-1-(tetrahydropyran-4-ylmethyl)-2,3-dihydro-1H-benzimidazole-5-sulfonic acid (4-ethylphenyl)isobutylamide Compound 2 | A | A |

TABLE 1-continued

| | | IC50 hRORg | IC50 hCD4/IL17 |
|---|---|---|---|
| 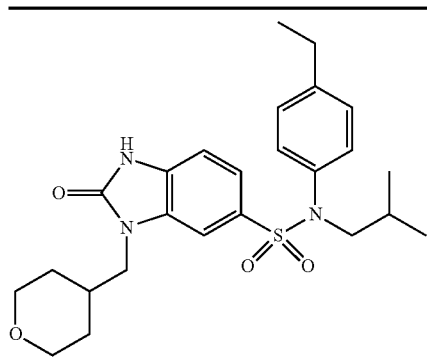 | 2-oxo-3-(tetrahydropyran-4-ylmethyl)-2,3-dihydro-1H-benzimidazole-5-sulfonic acid (4-ethylphenyl)isobutyl-amide<br>Compound 3 | B | A |

TABLE 2

| | | IC50 hRORg | IC50 hCD4/IL17 |
|---|---|---|---|
| 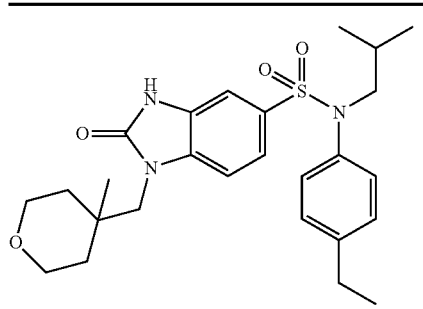 | 1-(4-methyltetrahydropyran-4-ylmethyl)-2-oxo-2,3-dihydro-1H-benzimidazole-5-sulfonic acid (4-ethylphenyl)isobutylamide<br>Compound 4 | A | A |
| 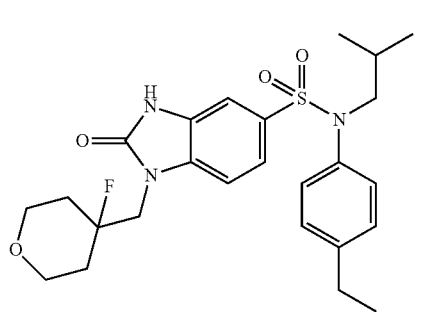 [SMILES: CCc1ccc(N(CC(C)C)S(=O)(=O)c2ccc3c(c2)[nH]c(=O)n3CC2(F)CCOCC2)cc1] | 1-(4-fluorotetrahydropyran-4-ylmethyl)-2-oxo-2,3-dihydro-1H-benzimidazole-5-sulfonic acid (4-ethylphenyl)isobutylamide<br>Compound 5 | A | A |
| 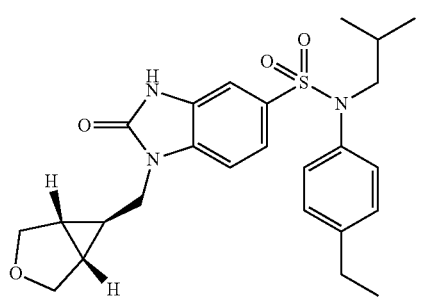 [SMILES: CCc1ccc(N(CC(C)C)S(=O)(=O)c2ccc3c(c2)[nH]c(=O)n3C[C@H]2[C@@H]3COC[C@@H]32)cc1] | 1-[(1R,5S,6S)-1-(3-oxabicyclo[3.1.0]hex-6-yl)methyl]-2-oxo-2,3-dihydro-1H-benzimidazole-5-sulfonic acid (4-ethylphenyl)isobutylamide<br>Compound 6 | A | ND |

TABLE 2-continued

| | IC50 hRORg | IC50 hCD4/IL17 |
|---|---|---|
| 1-oxetan-3-ylmethyl-2-oxo-2,3-dihydro-1H-benzimidazole-5-sulfonic acid (4-ethylphenyl)isobutylamide Compound 7 | A | A |
| 2-oxo-1-(2-oxo[1,3]dioxolan-4-ylmethyl)-2,3-dihydro-1H-benzimidazole-5-sulfonic acid (4-ethylphenyl)isobutylamide Compound 8 | A | ND |
| 2-oxo-1-(2-oxooxazolidin-5-ylmethyl)-2,3-dihydro-1H-benzimidazole-5-sulfonic acid (4-ethylphenyl)isobutylamide Compound 9 | C | ND |
| 2-oxo-1-pyridin-4-ylmethyl-2,3-dihydro-1H-benzimidazole-5-sulfonic acid (4-ethylphenyl)isobutylamide Compound 10 | B | A |
| 2-oxo-1-(tetrahydropyran-4-yl)-2,3-dihydro-1H-benzimidazole-5-sulfonic acid (4-ethylphenyl)isobutylamide Compound 11 | C | ND |

TABLE 2-continued

| | | IC50 hRORg | IC50 hCD4/IL17 |
|---|---|---|---|
| 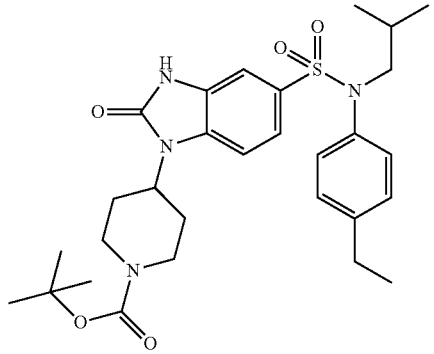 [SMILES: CCc1ccc(N(CC(C)C)S(=O)(=O)c2ccc3c(c2)[nH]c(=O)n3C2CCN(C(=O)OC(C)(C)C)CC2)cc1] | tert butyl ester of 4-{5-[(4-ethylphenyl)isobutyl-sulfamoyl]-2-oxo-2,3-dihydrobenzimidazol-1-yl}piperidine-1-carboxylic acid<br>Compound 12 | C | ND |
| 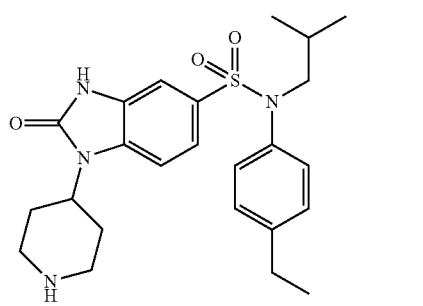 [SMILES: CCc1ccc(N(CC(C)C)S(=O)(=O)c2ccc3c(c2)[nH]c(=O)n3C2CCNCC2)cc1] | 2-oxo-1-piperidin-4-yl-2,3-dihydro-1H-benzimidazole-5-sulfonic acid (4-ethylphenyl)isobutylamide<br>Compound 13 | C | ND |
| 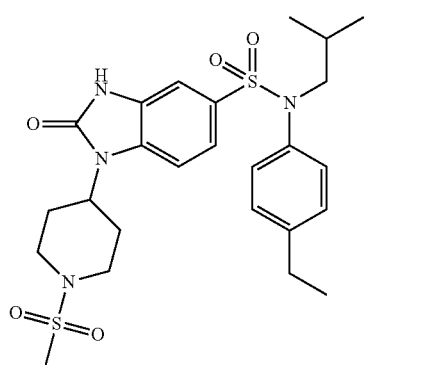 [SMILES: CCc1ccc(N(CC(C)C)S(=O)(=O)c2ccc3c(c2)[nH]c(=O)n3C2CCN(S(C)(=O)=O)CC2)cc1] | 1-(1-methanesulfonylpiperidin-4-yl)-2-oxo-2,3-dihydro-1H-benzimidazole-5-sulfonic acid (4-ethylphenyl)isobutylamide<br>Compound 14 | C | ND |
| 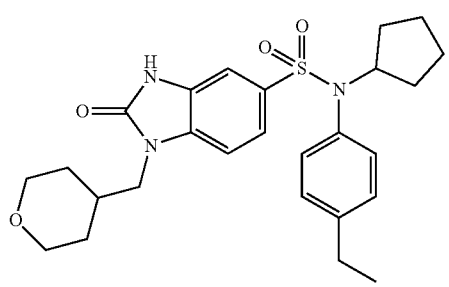 [SMILES: CCc1ccc(N(C2CCCC2)S(=O)(=O)c2ccc3c(c2)[nH]c(=O)n3CC2CCOCC2)cc1] | 2-oxo-1-(tetrahydropyran-4-ylmethyl)-2,3-dihydro-1H-benzimidazole-5-sulfonic acid (4-ethylphenyl)cyclopentylamide<br>Compound 15 | A | A |
| 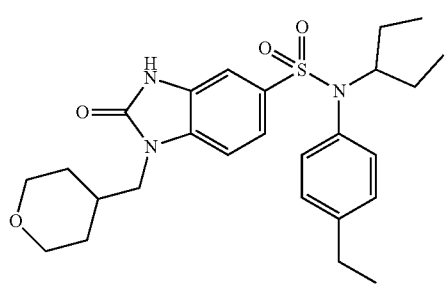 [SMILES: CCc1ccc(N(C(CC)CC)S(=O)(=O)c2ccc3c(c2)[nH]c(=O)n3CC2CCOCC2)cc1] | 2-oxo-1-(tetrahydropyran-4-ylmethyl)-2,3-dihydro-1H-benzimidazole-5-sulfonic acid (4-ethylphenyl)(1-ethylpropyl)amide<br>Compound 16 | A | A |

TABLE 2-continued

| | | IC50 hRORg | IC50 hCD4/IL17 |
|---|---|---|---|
| 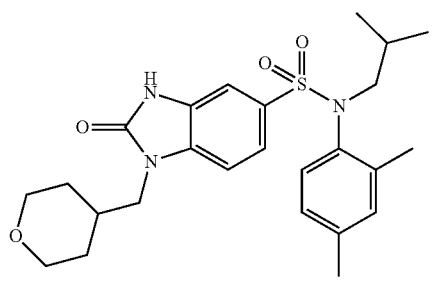 [SMILES: Cc1ccc(N(CC(C)C)S(=O)(=O)c2ccc3c(c2)[nH]c(=O)n3CC2CCOCC2)c(C)c1] | 2-oxo-1-(tetrahydropyran-4-ylmethyl)-2,3-dihydro-1H-benzimidazole-5-sulfonic acid (2,4-dimethylphenyl)isobutylamide<br>Compound 17 | A | A |
| 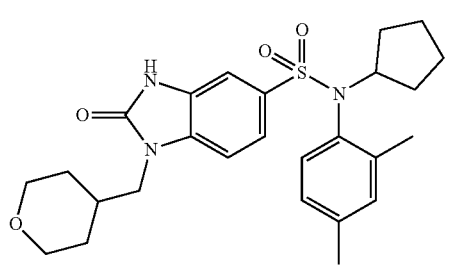 [SMILES: Cc1ccc(N(C2CCCC2)S(=O)(=O)c2ccc3c(c2)[nH]c(=O)n3CC2CCOCC2)c(C)c1] | 2-oxo-1-(tetrahydropyran-4-ylmethyl)-2,3-dihydro-1H-benzimidazole-5-sulfonic acid cyclopentyl(2,4-dimethylphenyl)amide<br>Compound 18 | A | A |
| 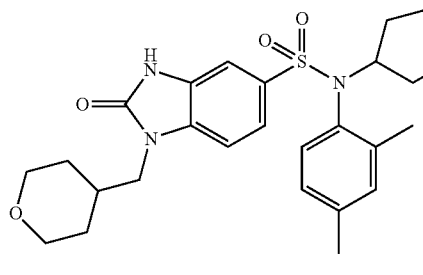 | 2-oxo-1-(tetrahydropyran-4-ylmethyl)-2,3-dihydro-1H-benzimidazole-5-sulfonic acid (2,4-dimethylphenyl)(1-ethylpropyl)amide<br>Compound 19 | A | A |
| 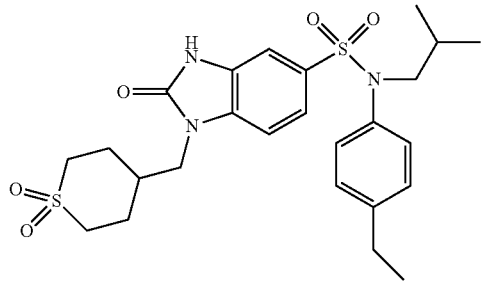 [SMILES: CCc1ccc(N(CC(C)C)S(=O)(=O)c2ccc3c(c2)[nH]c(=O)n3CC2CCS(=O)(=O)CC2)cc1] | 1-(1,1-dioxohexahydro-1$\lambda^6$-thiopyran-4-ylmethyl)-2-oxo-2,3-dihydro-1H-benzimidazole-5-sulfonic acid (4-ethylphenyl)isobutyl-amide<br>Compound 20 | A | A |
| 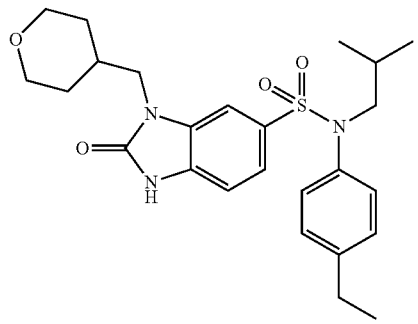 [SMILES: CCc1ccc(N(CC(C)C)S(=O)(=O)c2ccc3[nH]c(=O)n(CC4CCOCC4)c3c2)cc1] | 2-oxo-3-(tetrahydropyran-4-ylmethyl)-2,3-dihydro-1H-benzimidazole-5-sulfonic acid (4-ethylphenyl)isobutylamide<br>Compound 21 | B | B |

TABLE 2-continued

| | | IC50 hRORg | IC50 hCD4/IL17 |
|---|---|---|---|
| 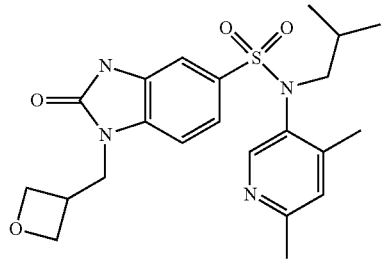 [SMILES: Cc1cc(C)c(N(CC(C)C)S(=O)(=O)c2ccc3c(c2)[nH]c(=O)n3CC2COC2)cn1] | 1-oxetan-3-ylmethyl-2-oxo-2,3-dihydro-1H-benzimidazole-5-sulfonic acid (4,6-dimethylpyridin-3-yl)isobutylamide Compound 22 | ND | ND |
| 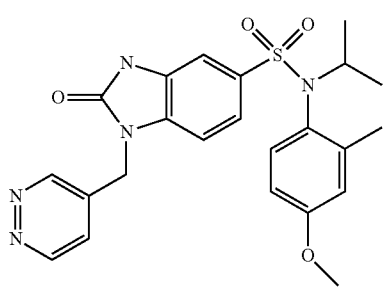 [SMILES: COc1ccc(N(C(C)C)S(=O)(=O)c2ccc3c(c2)[nH]c(=O)n3Cc2ccnnc2)c(C)c1] | 2-oxo-1-pyridazin-4-ylmethyl-2,3-dihydro-1H-benzimidazole-5-sulfonic acid isopropyl(4-methoxy-2-methylphenyl)amide Compound 23 | ND | ND |

ND: not determined;
A: IC50 < 100 nM.;
B: IC50 = 100 nM-1 µM;
C: IC50 > 1 µM

In the tables described above, the median inhibitory concentrations $IC_{50}$ for the compounds belonging to formula (I) according to the invention have been given according to the following models:

GAL4-RORγ Transactivation

The RORγ transactivation model was developed from the line HG5LN, which is a HeLa line that stably expresses a luciferase reporter gene controlled by a pentamer of the GAL4 recognition domain of yeast and of a β-globin promoter. The HG5LN line was stably transfected by the DNA-binding domain (DBD) of GAL4 fused to the ROR gamma ligand-binding domain (LBD). Molecules that inhibit the ROR gamma constitutive activity reduce the luciferase expression, thus leading to a reduction in the emitted luminescence.

The cells are seeded in 384-well plates (5000 cells in 45 µL/well of culture medium containing 10% fetal calf serum) and incubated for 4 hours at 37° C., 5% $CO_2$. 5 µL of the test molecules (compounds described in the tables described above) are then added to each well and the plates are incubated for 18 hours at a temperature of 37° C. under 5% of $CO_2$. 20 µL of luciferase substrate (Promega) are added to each well and the luminescence emitted is read by a microplate reader.

The luminescence units ("RLU") are normalized by positive controls ("POS" containing a saturated concentration of N-(2,2,2-trifluoroethyl)-N-[4-[2,2,2-trifluoro-1-hydroxy-1-(trifluoromethyl)ethyl]phenyl]benzenesulfonamide) and negative controls ("NEG" containing DMSO): % inhibition=((RLU-NEG)*100)/(POS-NEG). The IC50 values are calculated from a 4-parameter logistic model using the XLFit software (IDBS).

IL-17A Secretion

This model allows measurement of the effect of inhibitors on IL-17A secretion by CD4+ cells. The cells are frozen CD4+ cells (STEMCELL, #70026), isolated from peripheral human blood and activated with anti-CD3 and anti-CD28 antibodies. The amount of IL-17A secreted is measured by the TR-FRET (kit HTRF® Human Interleukin 17A (Cisbio, #64H17PEC)) technology.

The cells are rapidly thawed, resuspended in their culture medium (RPMI inactivated 10% FCS) supplemented with soluble anti-CD28 antibodies and seeded (100 000 cells/well) in 96-well plates precoated with anti-CD3 antibodies. The cells are then treated with the ranges of inhibitors to be tested (from 1000 nM to 0.05 nM, 0.1% DMSO). After 4 days of incubation, the HTRF signal is measured using a microplate reader (excitation=337 nm, λemission=620/665 nm). The ratios obtained (665/620) are normalized relative to the positive control (cells activated with anti-CD3 and anti-CD28, 0.1% DMSO). The $IC_{50}$ values are calculated from a 4-parameter logistic model using the XLFit software (IDBS).

Preferentially, the compounds of formula (I) according to the invention are chosen from the following compounds:

TABLE 3

| Structure | Name |
|---|---|
| (structure) | 2-oxo-1-(tetrahydropyran-4-ylmethyl)-2,3-dihydro-1H-benzimidazole-5-sulfonic acid (4-ethylphenyl)isobutylamide<br>Compound 2 |
| (structure) | 1-(4-methyltetrahydropyran-4-ylmethyl)-2-oxo-2,3-dihydro-1H-benzimidazole-5-sulfonic acid (4-ethylphenyl)isobutylamide<br>Compound 4 |
| (structure) | 1-(4-fluorotetrahydropyran-4-ylmethyl)-2-oxo-2,3-dihydro-1H-benzimidazole-5-sulfonic acid (4-ethylphenyl)isobutylamide<br>Compound 5 |
| (structure) | 1-[(1R,5S,6S)-1-(3-oxabicyclo[3.1.0]hex-6-yl)methyl]-2-oxo-2,3-dihydro-1H-benzimidazole-5-sulfonic acid (4-ethylphenyl)isobutylamide<br>Compound 6 |
| (structure) | 1-oxetan-3-ylmethyl-2-oxo-2,3-dihydro-1H-benzimidazole-5-sulfonic acid (4-ethylphenyl)isobutylamide<br>Compound 7 |

TABLE 3-continued

| Structure | Name |
|---|---|
| (structure) | 2-oxo-1-(2-oxo[1,3]dioxolan-4-ylmethyl)-2,3-dihydro-1H-benzimidazole-5-sulfonic acid (4-ethylphenyl)isobutylamide<br>Compound 8 |
| (structure) | 2-oxo-1-pyridin-4-ylmethyl-2,3-dihydro-1H-benzimidazole-5-sulfonic acid (4-ethylphenyl)isobutylamide<br>Compound 10 |
| (structure) | 2-oxo-1-(tetrahydropyran-4-ylmethyl)-2,3-dihydro-1H-benzimidazole-5-sulfonic acid (4-ethylphenyl)cyclopentylamide<br>Compound 15 |
| (structure) | 2-oxo-1-(tetrahydropyran-4-ylmethyl)-2,3-dihydro-1H-benzimidazole-5-sulfonic acid (4-ethylphenyl)(1-ethylpropyl)amide<br>Compound 16 |
| (structure) | 2-oxo-1-(tetrahydropyran-4-ylmethyl)-2,3-dihydro-1H-benzimidazole-5-sulfonic acid (2,4-dimethylphenyl)isobutylamide<br>Compound 17 |

TABLE 3-continued

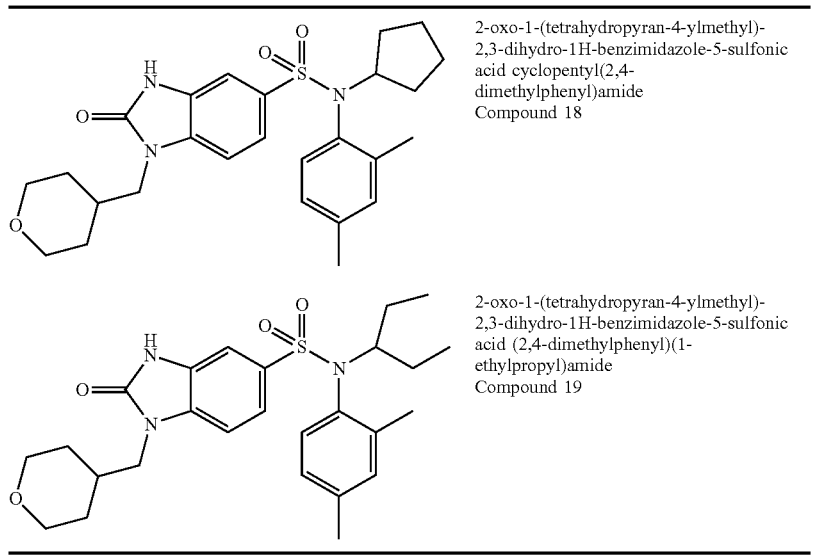

| | |
|---|---|
| | 2-oxo-1-(tetrahydropyran-4-ylmethyl)-2,3-dihydro-1H-benzimidazole-5-sulfonic acid cyclopentyl(2,4-dimethylphenyl)amide<br>Compound 18 |
| | 2-oxo-1-(tetrahydropyran-4-ylmethyl)-2,3-dihydro-1H-benzimidazole-5-sulfonic acid (2,4-dimethylphenyl)(1-ethylpropyl)amide<br>Compound 19 |

Thus, compounds 2, 4 to 8, 10 and 15 to 19 are preferred.

The invention also relates to the compound(s) as described previously, as medicament and cosmetic.

Preferably, the invention also relates to the compound(s) as described previously, as medicament.

Specifically, the compounds according to the invention have advantageous pharmacological properties, given that said compounds modulate, i.e. inhibit, the activity of the RORγt receptor.

Thus, these properties make the compound(s) of formula (I) as described previously usable as medicament in the treatment of diseases mediated by the RORγt receptor.

Preferably, the compound(s) according to the invention are used in the treatment of inflammatory disorders and/or autoimmune diseases mediated by the RORγt receptor.

More preferably, the compound(s) according to the invention, preferably those chosen from the compounds corresponding to formula (I), are used in the treatment of acne, psoriasis and/or atopic dermatitis.

According to another embodiment, the compounds according to the invention are used for cosmetic treatment of the skin.

As indicated above, the present invention also relates to a pharmaceutical composition comprising, in a pharmaceutically acceptable medium, one or more compounds of formula (I) as defined previously, pharmaceutically acceptable addition salts thereof, hydrates thereof and/or solvates thereof.

More preferably, the pharmaceutical composition comprises one or more compounds of formula (I) chosen from compounds (1) to (20) defined previously.

Even more preferentially, the pharmaceutical composition comprises one or more compounds of formula (I) chosen from compounds 2, 4 to 8, 10 and 15 to 19.

The pharmaceutical composition according to the invention as described previously may be administered orally or topically.

Preferably, the pharmaceutical composition is conditioned in a form that is suitable for topical application.

Via the oral route, the composition may be in the form of tablets, gel capsules, coated tablets, syrups, suspensions, solutions, powders, granules, emulsions, suspensions of microspheres, nanospheres or lipid or polymeric vesicles allowing controlled release.

Via the topical route, the pharmaceutical composition according to the invention is more particularly intended for treating the skin and mucous membranes, and may be in liquid, pasty or solid form, and more particularly in the form of ointments, creams, milks, pomades, powders, impregnated pads, syndets, solutions, gels, sprays, mousses, suspensions, sticks, shampoos or washing bases. They may also be in the form of suspensions of microspheres or nanospheres or lipid or polymeric vesicles or of polymeric or gelled patches allowing controlled release.

The pharmaceutical composition is used for treating inflammatory disorders and/or autoimmune diseases mediated by the RORγt receptor.

More preferentially, the pharmaceutical composition is used in the treatment of acne and/or psoriasis.

The invention also relates to a process for treating diseases mediated by the RORγt receptor, comprising the administration, especially topically or orally, of a therapeutically effective amount of the pharmaceutical composition as defined above to a patient.

Preferably, the pharmaceutical composition is applied topically.

Preferentially, a subject of the invention is the compound(s) of formula (I) for their use in the treatment of acne.

As a variant, a subject of the invention is also the compound(s) of formula (I) for their use in the treatment of psoriasis.

Alternatively, the compound(s) of formula (I) according to the invention are used for cosmetic treatment of the skin.

The invention also relates to the pharmaceutical composition as defined above for its use in the treatment of inflammatory disorders and/or autoimmune diseases mediated by the RORγt receptor, in particular acne and/or psoriasis.

The examples that follow serve to illustrate the invention without, however, being limiting in nature.

EXAMPLES

The standard LCMS method for analyzing the products is as follows: BEH $C_{18}$ standard column (150×2.1 mm, 1.8 μm) solvent: water/acetonitrile 0.1% formic acid.

The preparative HPLC purifications were performed on a $C_{18}$ column using, as eluent: 85% acetonitrile in water/0.1% formic acid.

Part I: Synthesis of the Bicyclic Sulfonamides Via Reaction Scheme 1

Reaction scheme 1

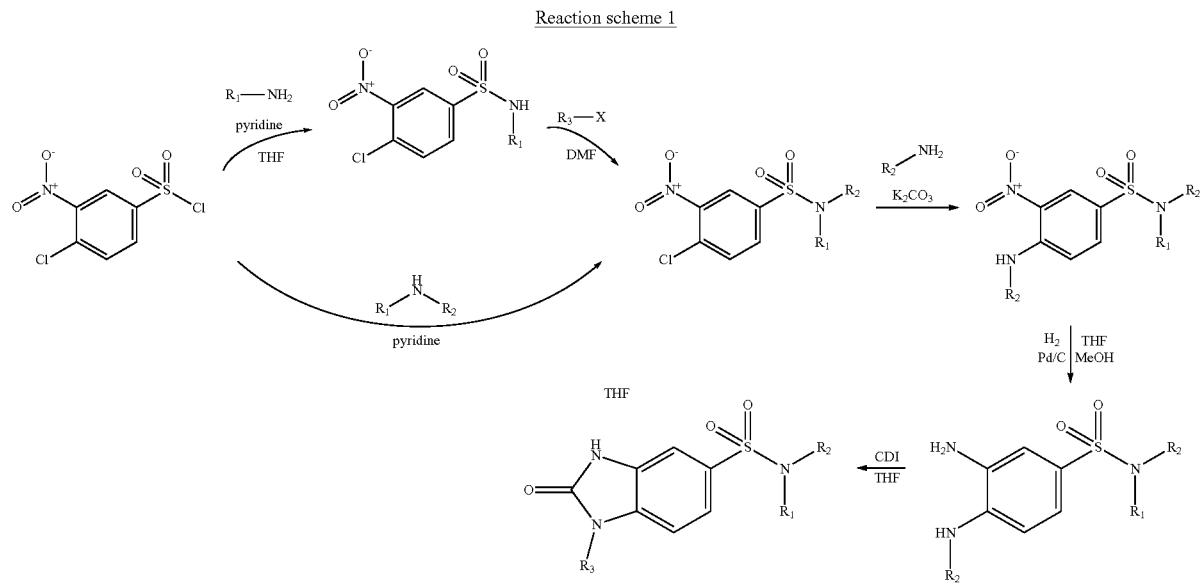

Example 1: Synthesis of 2-oxo-1-(tetrahydropyran-4-ylmethyl)-2,3-dihydro-1H-benzimidazole-5-sulfonic acid (4-ethylphenyl)isobutylamide Compound 2

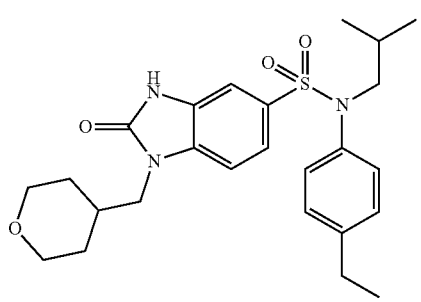

1. Synthesis of Intermediate 1.1

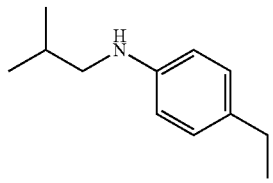

(4-Ethylphenyl)isobutylamine

Isobutyraldehyde (6.33 ml; 0.07 mol) in tetrahydrofuran (100 ml) is added to 4-ethylaniline (9.48 ml; 0.08 mol). The mixture is stirred for 2 hours at room temperature. Sodium triacetoxyborohydride (22.04 g; 0.10 mol) is then added. The mixture is stirred overnight at room temperature, water (100 ml) is added and the resulting mixture is extracted with ethyl acetate (2×100 ml). The organic phases are combined, washed with brine (100 ml), dried over $Na_2SO_4$ and concentrated.

The crude product is chromatographed on silica gel (eluent: heptane/dichloromethane from 0 to 50% of dichloromethane). The (4-ethylphenyl)isobutylamine is obtained in the form of an orange oil with a compliant $^1$H NMR.
MS: [M+H]=179

2. Synthesis of Intermediate 1.1

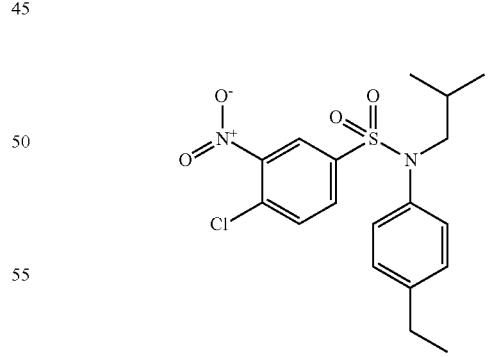

4-Chloro-N-(4-ethylphenyl)-N-isobutyl-3-nitrobenzenesulfonamide

Pyridine (1.85 ml; 22.96 mmol) and 4-chloro-3-nitrobenzenesulfonyl chloride (1.0 g; 3.83 mmol) are added to a solution of (4-ethylphenyl)isobutylamine (0.68 g; 3.83 mmol) in tetrahydrofuran (15 ml).

The mixture is stirred for 3 hours, hydrolyzed and extracted with ethyl acetate. The organic phase is dried over anhydrous $Na_2SO_4$, filtered and concentrated.

The crude product is chromatographed on silica gel (eluent: heptane/ethyl acetate, from 0 to 20% of ethyl acetate). The 4-chloro-N-(4-ethylphenyl)-N-isobutyl-3-nitrobenzenesulfonamide (1.42 g; 93%) is obtained in the form of a yellow solid with a compliant $^1$H NMR.

MS: [M+H]=397

3. Synthesis of Intermediate 1.3

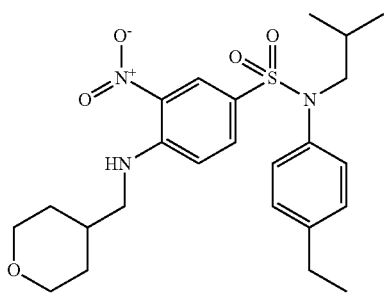 [SMILES: CCc1ccc(N(CC(C)C)S(=O)(=O)c2ccc(NCC3CCOCC3)c([N+](=O)[O-])c2)cc1]

N-(4-ethylphenyl)-N-isobutyl-3-nitro-4-[(tetrahydropyran-4-ylmethyl)amino]benzenesulfonamide A mixture of 4-chloro-N-(4-ethylphenyl)-N-isobutyl-3-nitrobenzenesulfonamide (0.98 g; 2.47 mmol), 4-aminomethyltetrahydropyran (0.30 g; 2.59 mmol) and potassium carbonate (0.50 g; 3.62 mmol) in N,N-dimethylformamide (5 ml) is stirred for 4 hours at 60° C., hydrolyzed and extracted with ethyl acetate. The organic phase is dried ($Na_2SO_4$), filtered and concentrated. The crude product is chromatographed on silica gel (eluent: heptane/ethyl acetate, from 10 to 50% of ethyl acetate). The N-(4-ethylphenyl)-N-isobutyl-3-nitro-4-[(tetrahydropyran-4-ylmethyl)amino]benzenesulfonamide (0.99 g; 84%) is obtained in the form of a yellow solid with a compliant $^1$H NMR.

MS: [M+H]=476

4. Synthesis of Intermediate 1.4

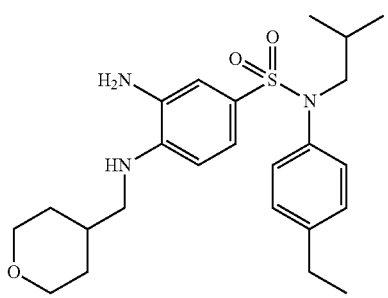 [SMILES: CCc1ccc(N(CC(C)C)S(=O)(=O)c2ccc(NCC3CCOCC3)c(N)c2)cc1]

3-amino-N-(4-ethylphenyl)-N-isobutyl-4-[(tetrahydropyran-4-ylmethyl)amino]benzenesulfonamide 10% Pd/C (50% $H_2O$) (3.46 g; 1.63 mmol) is added to a suspension of N-(4-ethylphenyl)-N-isobutyl-3-nitro-4-[(tetrahydropyran-4-ylmethyl)amino]benzenesulfonamide (19.82 g; 32.50 mmol) in tetrahydrofuran (120 ml) and methanol (120 ml).

The reaction medium is stirred overnight under a hydrogen atmosphere and filtered through Celite, which is rinsed several times with a DCM/tetrahydrofuran/MeOH mixture.

The filtrate is concentrated, taken up in pentane and filtered. The solid obtained is rinsed again with pentane, and then once more with a mixture of pentane and a small amount of ethyl ether. The 3-amino-N-(4-ethylphenyl)-N-isobutyl-4-[(tetrahydropyran-4-ylmethyl)amino]benzenesulfonamide (11.77 g; 81%) is obtained in the form of a beige-colored solid with a compliant $^1$H NMR.

MS: [M+H]=446

5. Synthesis of Compound 2 According to the Invention

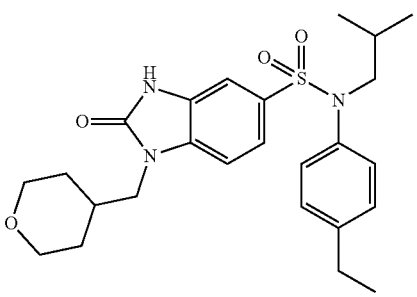 [SMILES: CCc1ccc(N(CC(C)C)S(=O)(=O)c2ccc3c(c2)[nH]c(=O)n3CC2CCOCC2)cc1]

3-Amino-N-(4-ethylphenyl)-N-isobutyl-4-[(tetrahydropyran-4-ylmethyl)amino]benzenesulfonamide (1.00 g, 2.24 mmol) is dissolved in tetrahydrofuran (10 ml), followed by addition of N,N'-carbonyldiimidazole (1.09 g; 6.72 mmol). The reaction medium is stirred for 2 hours at room temperature, hydrolyzed and extracted with ethyl acetate. The organic phases are combined, washed with saturated $NaHCO_3$ solution and with water, and then dried ($MgSO_4$), filtered and concentrated.

The crude product is chromatographed on silica gel (eluent: dichloromethane/methanol, from 0 to 8% of methanol). The 2-oxo-1-(tetrahydropyran-4-ylmethyl)-2,3-dihydro-1H-benzimidazole-5-sulfonic acid (4-ethylphenyl) isobutylamide (785 mg; 74%) is obtained in the form of an off-white crystalline solid by recrystallization from an acetone/water mixture.

$^1$H NMR (DMSO-$d_6$) δ: 0.83 (d, J=6.5 Hz, 6H), 1.17 (t, J=7.6 Hz, 3H), 1.28 (qd, J=12.2, 4.4 Hz, 2H), 1.39 (p, J=6.7 Hz, 1H), 1.47 (d, J=12.2 Hz, 2H), 2.00 (d, J=12.5 Hz, 1H), 2.59 (q, J=7.6 Hz, 2H), 3.21 (d, J=11.3 Hz, 2H), 3.26 (d, J=6.6 Hz, 2H), 3.72 (d, J=7.2 Hz, 2H), 3.82 (dd, J=12.2, 3.8 Hz, 2H), 6.96 (d, J=8.0 Hz, 2H), 7.00 (s, 1H), 7.17 (d, J=7.9 Hz, 2H), 7.20 (d, J=8.3 Hz, 1H), 7.33 (d, J=8.3 Hz, 1H), 11.16 (s, 1H)

MS: [M+H]=472

Example 2: Synthesis of 1-(4-methyltetrahydropyran-4-ylmethyl)-2-oxo-2,3-dihydro-1H-benzimidazole-5-sulfonic acid (4-ethylphenyl)isobutylamide 1. Synthesis of Intermediate 2.1

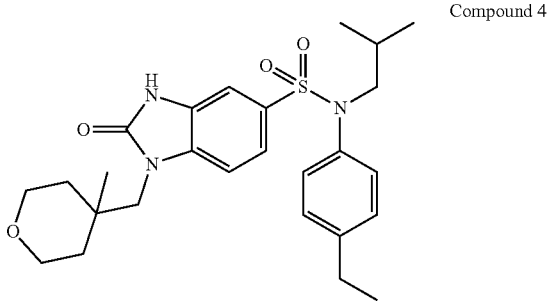 [SMILES: CCc1ccc(N(CC(C)C)S(=O)(=O)c2ccc3c(c2)[nH]c(=O)n3CC2(C)CCOCC2)cc1]

Compound 4

N-(4-ethylphenyl)-N-isobutyl-4-[(4-methyltetrahydropyran-4-ylmethyl)amino]-3-nitrobenzenesulfonamide With a procedure similar to that described for intermediate 1.3, N-(4-ethylphenyl)-N-isobutyl-4-[(4-methyltetrahydropyran-4-ylmethyltetrahydropyran-4-ylmethyl)amino]-3-nitrobenzenesulfonamide (100 mg; 27%) is obtained in the form of a yellow oil with a compliant ¹H NMR.

MS: [M+H]=490

2. Synthesis of Intermediate 2.2

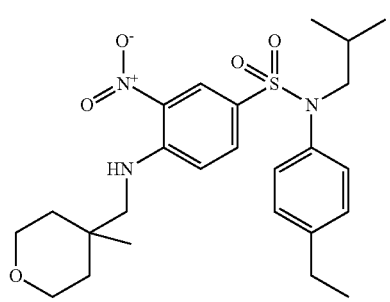 [SMILES: CCc1ccc(N(CC(C)C)S(=O)(=O)c2ccc(NCC3(C)CCOCC3)c([N+](=O)[O-])c2)cc1]

3-amino-N-(4-ethylphenyl)-N-isobutyl-4-[(4-methyltetrahydropyran-4-ylmethyl)amino]benzenesulfonamide With a procedure similar to that described for intermediate 1.4, 3-amino-N-(4-ethylphenyl)-N-isobutyl-4-[(4-methyltetrahydropyran-4-ylmethyl)amino]benzenesulfonamide (80 mg; 85%) is obtained in the form of a brown oil with a compliant ¹H NMR.

MS: [M+H]=460

3. Synthesis of Compound 4 (Compound 269) According to the Invention

With a procedure similar to that described in example 1, 1-(4-methyltetrahydropyran-4-ylmethyl)-2-oxo-2,3-dihydro-1H-benzimidazole-5-sulfonic acid (4-ethylphenyl)isobutylamide (40 mg; 43%) is obtained in the form of a beige-colored solid.

¹H NMR (DMSO-d6) δ: 0.84 (d, J=6.7 Hz, 6H), 1.03 (s, 3H), 1.18 (t, J=7.6 Hz, 3H), 1.27 (d, J=13.7 Hz, 2H), 1.40 (p, J=6.8 Hz, 1H), 1.59 (s, 1H), 1.59 (dd, J=23.5, 4.4 Hz, 1H), 2.53-2.66 (m, 3H), 3.27 (d, J=7.3 Hz, 2H), 3.51 (t, J=9.8 Hz, 2H), 3.64-3.74 (m, 4H), 6.93-7.04 (m, 3H), 7.14-7.24 (m, 3H), 7.35 (d, J=8.4 Hz, 1H), 11.21 (s, 1H).

MS: [M+H]=486

Example 3: Synthesis of 1-(4-fluorotetrahydropyran-4-ylmethyl)-2-oxo-2,3-dihydro-1H-benzimidazole-5-sulfonic acid (4-ethylphenyl)isobutylamide

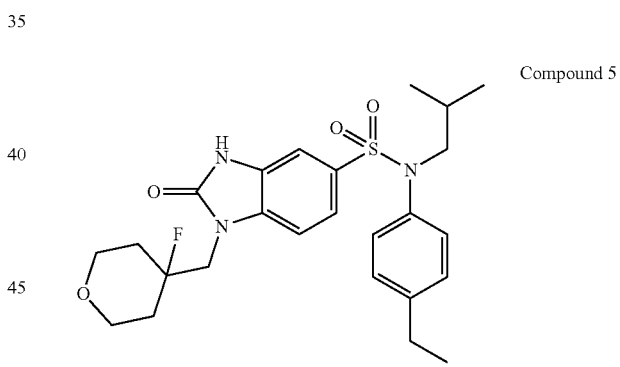

Compound 5

1. Synthesis of Intermediate 3.1

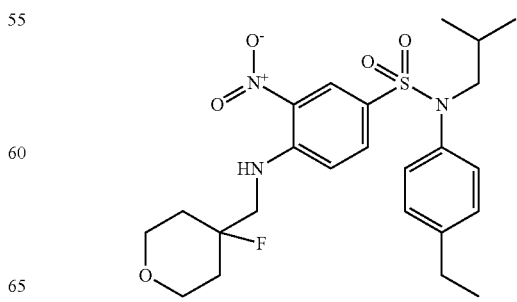

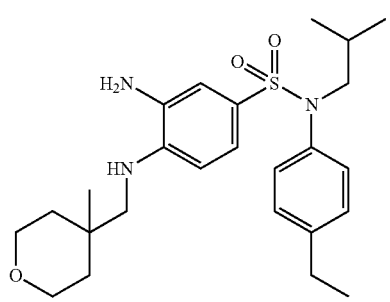 [SMILES: CCc1ccc(N(CC(C)C)S(=O)(=O)c2ccc(NCC3(C)CCOCC3)c(N)c2)cc1]

N-(4-ethylphenyl)-4-[(4-fluorotetrahydropyran-4-ylmethyl)amino]-N-isobutyl-3-nitrobenzenesulfonamide A mixture of 4-chloro-N-(4-ethylphenyl)-N-(1-ethylpropyl)-3-nitrobenzenesulfonamide (200 mg; 0.50 mmol), N,N-dimethylformamide (2.00 ml), potassium carbonate (77 mg; 0.55 mmol) and (4-fluorooxan-4-yl)methanamine (70.46 mg; 0.53 mmol) is stirred for 2 hours at a temperature of 40° C., diluted with ethyl acetate. The organic phase is washed with saturated NH$_4$Cl solution and with water, dried (MgSO$_4$), filtered and concentrated to dryness. The N-(4-ethylphenyl)-4-[(4-fluorotetrahydropyran-4-ylmethyl)amino]-N-isobutyl-3-nitrobenzenesulfonamide (205 mg; 82%) is obtained in the form of a clear oil with a compliant $^1$H NMR.

MS: [M+H]=494

2. Synthesis of Intermediate 3.2

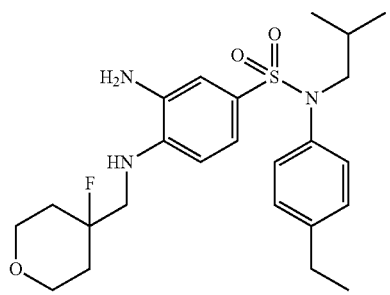 [SMILES: CCc1ccc(N(CC(C)C)S(=O)(=O)c2ccc(NCC3(F)CCOCC3)c(N)c2)cc1]

3-amino-N-(4-ethylphenyl)-4-[(4-fluorotetrahydropyran-4-ylmethyl)amino]-N-isobutylbenzenesulfonamide With a procedure similar to that described for intermediate 1.4, 3-amino-N-(4-ethylphenyl)-4-[(4-fluorotetrahydropyran-4-ylmethyl)amino]-N-isobutylbenzenesulfonamide (190 mg; 99%) is obtained in the form of a colorless oil with a compliant $^1$H NMR.

MS: [M+H]=465

3. Synthesis of Compound 5 According to the Invention

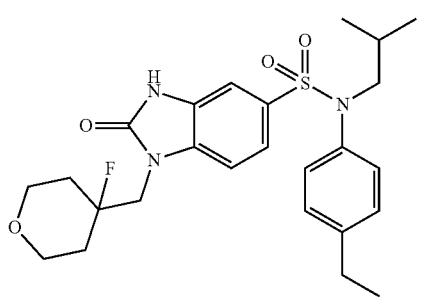 [SMILES: CCc1ccc(N(CC(C)C)S(=O)(=O)c2ccc3c(c2)[nH]c(=O)n3CC2(F)CCOCC2)cc1]

With a procedure similar to that described in example 1, 1-(4-fluorotetrahydropyran-4-ylmethyl)-2-oxo-2,3-dihydro-1H-benzimidazole-5-sulfonic acid (4-ethylphenyl)isobutylamide (80 mg; 40%) is obtained in the form of a white crystalline solid.

$^1$H NMR (DMSO-d6) δ: 0.84 (d, J=6.7 Hz, 6H), 1.18 (t, J=7.6 Hz, 3H), 1.40 (p, J=6.8 Hz, 2H), 1.69 (t, J=12.4 Hz, 2H), 1.74-1.94 (m, 1H), 2.61 (q, J=7.6 Hz, 2H), 3.27 (d, J=7.3 Hz, 2H), 3.52 (t, J=10.7 Hz, 2H), 3.76 (d, J=11.7 Hz, 2H), 4.08 (d, J=22.1 Hz, 2H), 6.97-7.00 (m, 2H), 7.02 (d, J=1.7 Hz, 1H), 7.18 (d, J=8.3 Hz, 2H), 7.26 (td, J=8.2, 1.7 Hz, 2H), 11.25 (s, 1H).

MS: [M+H]=490

Example 4: Synthesis of 1-[(1R,5S,6S)-1-(3-oxabicyclo[3.1.0]hex-6-yl)methyl]-2-oxo-2,3-dihydro-1H-benzimidazole-5-sulfonic acid (4-ethylphenyl)isobutylamide

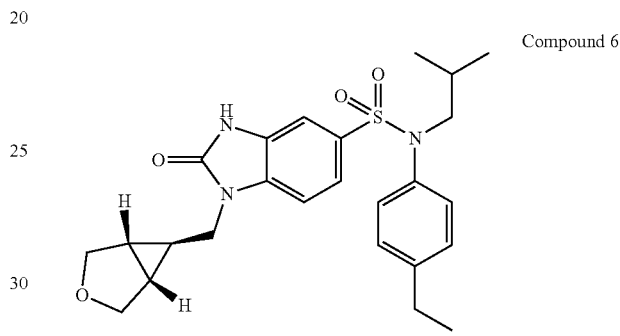

Compound 6

1. Synthesis of Intermediate 4.1

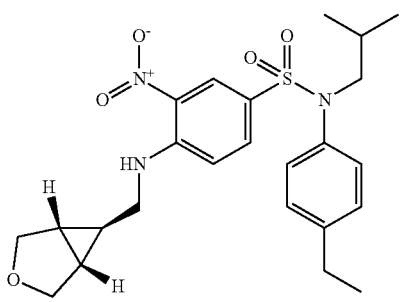 [SMILES: CCc1ccc(N(CC(C)C)S(=O)(=O)c2ccc(NC[C@@H]3[C@H]4COC[C@@H]34)c([N+](=O)[O-])c2)cc1]

N-(4-ethylphenyl)-N-isobutyl-3-nitro-4-{[(1R,5S,6S)—1-(3-oxabicyclo[3.1.0]hex-6-yl)methyl]amino}benzenesulfonamide With a procedure similar to that described for intermediate 1.3, N-(4-ethylphenyl)-N-isobutyl-3-nitro-4-{[(1R,5S,6S)-1-(3-oxabicyclo[3.1.0]hex-6-yl)methyl]amino}benzenesulfonamide (238 mg; 100%) is obtained in the form of a yellow solid with a compliant $^1$H NMR.

MS: [M+H]=474

2. Synthesis of Intermediate 4.2

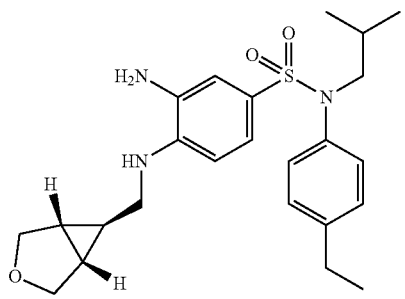 [SMILES: CCc1ccc(N(CC(C)C)S(=O)(=O)c2ccc(NC[C@@H]3[C@H]4COC[C@@H]34)c(N)c2)cc1]

3-amino-N-(4-ethylphenyl)-N-isobutyl-4-{[(1R,5S,6S)-1-(3-oxabicyclo[3.1.0]hex-6-yl)methyl]amino}benzenesulfonamide With a procedure similar to that described for intermediate 1.4, 3-amino-N-(4-ethylphenyl)-N-isobutyl-4-{[(1R,5S,6S)-1-(3-oxabicyclo[3.1.0]hex-6-yl)methyl]amino}benzenesulfonamide (206 mg; 94%) is obtained in the form of a brown oil with a compliant $^1$H NMR.

MS: [M+H]=444

3. Synthesis of Compound 6 According to the Invention

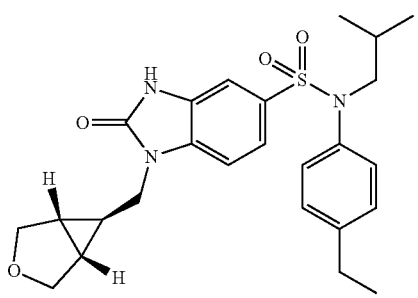 [SMILES: CCc1ccc(N(CC(C)C)S(=O)(=O)c2ccc3c(c2)[nH]c(=O)n3C[C@H]2[C@@H]3COC[C@@H]32)cc1]

With a procedure similar to that described in example 1, 1-[(1R,5S,6S)-1-(3-oxabicyclo[3.1.0]hex-6-yl)methyl]-2-oxo-2,3-dihydro-1H-benzimidazole-5-sulfonic acid (4-ethylphenyl)isobutylamide (56 mg; 25%) is obtained in the form of an off-white crystalline solid.

$^1$H NMR (DMSO-d6) δ: 0.84 (d, J=6.7 Hz, 6H), 1.06 (dt, J=7.1, 3.6 Hz, 1H), 1.18 (t, J=7.6 Hz, 3H), 1.40 (dt, J=13.6, 6.7 Hz, 1H), 1.75 (t, J=2.6 Hz, 2H), 2.60 (q, J=7.6 Hz, 2H), 3.25-3.30 (m, 2H), 3.53 (d, J=8.3 Hz, 2H), 3.68 (d, J=8.4 Hz, 2H), 3.79 (d, J=7.1 Hz, 2H), 6.97 (d, J=8.3 Hz, 2H), 7.02 (d, J=1.8 Hz, 1H), 7.18 (d, J=8.3 Hz, 2H), 7.23 (dd, J=8.3, 1.8 Hz, 1H), 7.37 (d, J=8.3 Hz, 1H), 11.14 (s, 1H).

MS: [M+H]=470

Example 5: Synthesis of 1-oxetan-3-ylmethyl-2-oxo-2,3-dihydro-1H-benzimidazole-5-sulfonic acid (4-ethylphenyl)isobutylamide Compound 7

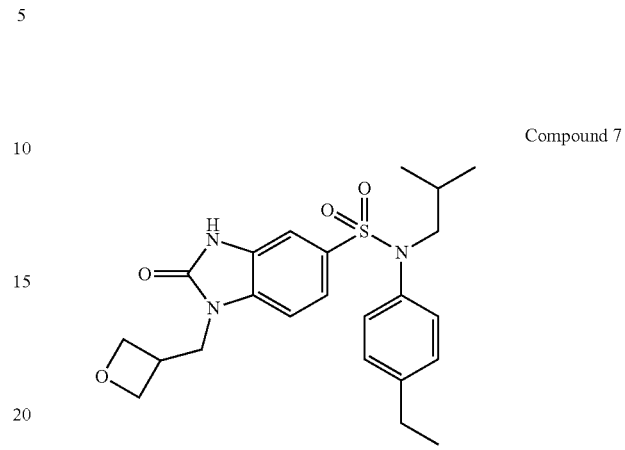

1. Synthesis of Intermediate 5.1

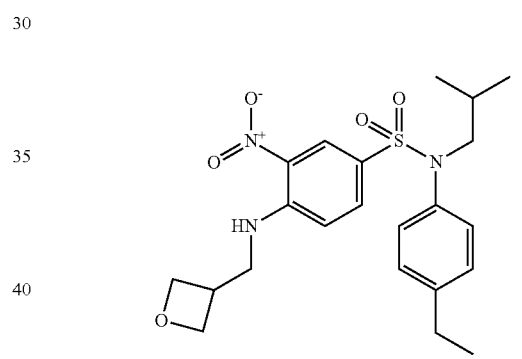

N-(4-ethylphenyl)-N-isobutyl-3-nitro-4-[(oxetan-3-ylmethyl)amino]benzenesulfonamide A mixture of 4-chloro-N-(4-ethylphenyl)-N-isobutyl-3-nitrobenzenesulfonamide (500 mg; 1.26 mmol), 1-methyl-2-pyrrolidone (5 ml), cesium carbonate (1.03 g; 3.15 mmol) and methyloxetane-3-ammonium hydrochloride (187 mg; 1.51 mmol) is stirred for 2 hours at room temperature and diluted with ethyl acetate (20 ml).

The organic phase is washed with saturated NH$_4$Cl solution (20 ml), with saturated NaHCO$_3$ solution (20 ml) and with water (20 ml), dried (MgSO$_4$), filtered and concentrated to dryness.

The N-(4-ethylphenyl)-N-isobutyl-3-nitro-4-[(oxetan-3-ylmethyl)amino]benzenesulfonamide (520 mg; 92%) is obtained in the form of a yellow oil with a compliant $^1$H NMR.

MS: [M+H]=450

2. Synthesis of Intermediate 5.2

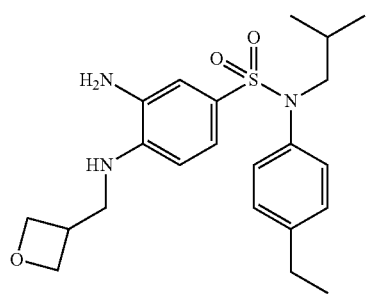 [SMILES: CCc1ccc(N(CC(C)C)S(=O)(=O)c2ccc(NCC3COC3)c(N)c2)cc1]

3-amino-N-(4-ethylphenyl)-N-isobutyl-4-[(oxetan-3-ylmethyl)amino]benzenesulfonamide With a procedure similar to that described for intermediate 1.4, 3-amino-N-(4-ethylphenyl)-N-isobutyl-4-[(oxetan-3-ylmethyl)amino]benzenesulfonamide (90 mg; 19%) is obtained in the form of an oil with a compliant $^1$H NMR.

MS: [M+H]=419

3. Synthesis of Compound 7 According to the Invention

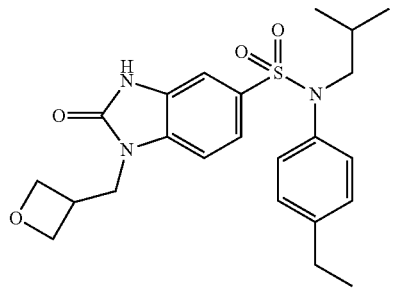 [SMILES: CCc1ccc(N(CC(C)C)S(=O)(=O)c2ccc3c(c2)[nH]c(=O)n3CC2COC2)cc1]

With a procedure similar to that described for example 1, 1-oxetan-3-ylmethyl-2-oxo-2,3-dihydro-1H-benzimidazole-5-sulfonic acid (4-ethylphenyl)isobutylamide (50 mg; 52%) is obtained in the form of a beige-colored solid.

$^1$H NMR (DMSO-d6) δ: 0.84 (d, J=6.7 Hz, 6H), 1.18 (t, J=7.6 Hz, 3H), 1.40 (hept, J=6.7 Hz, 1H), 2.60 (q, J=7.6 Hz, 2H), 3.26 (d, J=7.3 Hz, 2H), 4.15 (d, J=7.2 Hz, 2H), 4.42 (t, J=6.1 Hz, 2H), 4.63 (t, J=7.0 Hz, 2H), 6.92-7.05 (m, 3H), 7.18 (d, J=7.9 Hz, 2H), 7.23 (d, J=8.3 Hz, 1H), 7.37 (d, J=8.3 Hz, 1H).

MS: [M+H]=444

Example 6: Synthesis of 2-oxo-1-(2-oxo[1,3]dioxolan-4-ylmethyl)-2,3-dihydro-1H-benzimidazole-5-sulfonic acid (4-ethylphenyl)isobutylamide

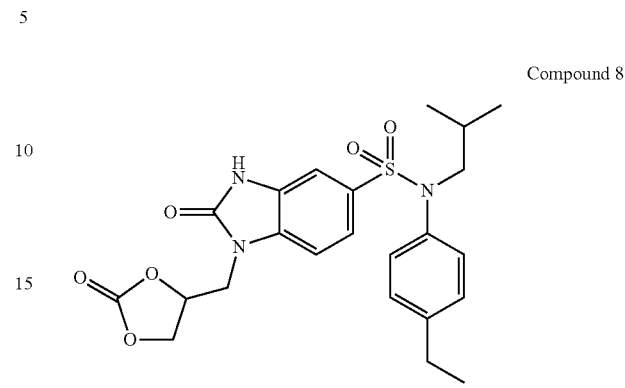

Compound 8

1. Synthesis of Intermediate 6.1

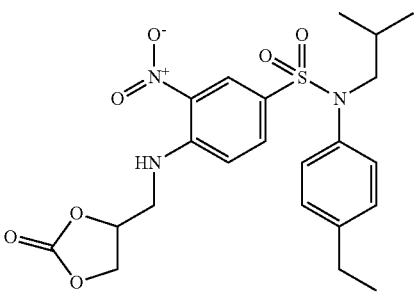 [SMILES: CCc1ccc(N(CC(C)C)S(=O)(=O)c2ccc(NCC3COC(=O)O3)c([N+](=O)[O-])c2)cc1]

N-(4-ethylphenyl)-N-isobutyl-3-nitro-4-[(2-oxo[1,3]dioxolan-4-ylmethyl)amino]benzenesulfonamide With a procedure similar to that described for intermediate 1.3, N-(4-ethylphenyl)-N-isobutyl-3-nitro-4-[(2-oxo[1,3]dioxolan-4-ylmethyl)amino]benzenesulfonamide (300 mg; 100%) is obtained in the form of a brown oil with a compliant $^1$H NMR.

MS: [M+H]=478

2. Synthesis of Intermediate 6.2

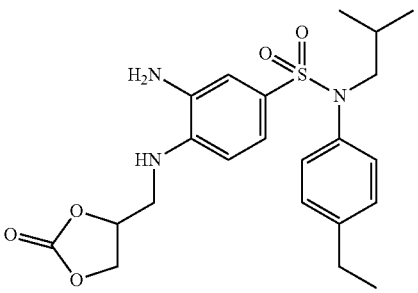 [SMILES: CCc1ccc(N(CC(C)C)S(=O)(=O)c2ccc(NCC3COC(=O)O3)c(N)c2)cc1]

3-amino-N-(4-ethylphenyl)-N-isobutyl-4-[(2-oxo-[1,3]dioxolan-4-ylmethyl)amino]benzenesulfonamide With a procedure similar to that described for intermediate 1.4, 3-amino-N-(4-ethylphenyl)-N-isobutyl-4-[(2-oxo[1,3,]dioxolan-4-ylmethyl)amino]benzenesulfonamide (286 mg; 100%) is obtained in the form of a pale yellow oil with a compliant $^1$H NMR.

MS: [M+H]=448

3. Synthesis of Compound 8 According to the Invention

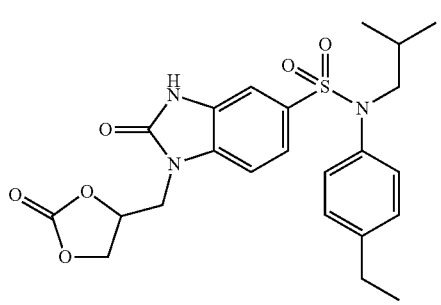 [SMILES: CCc1ccc(N(CC(C)C)S(=O)(=O)c2ccc3c(c2)[nH]c(=O)n3CC2COC(=O)O2)cc1]

With a procedure similar to that described for example 1, 2-oxo-1-(2-oxo[1,3]dioxolan-4-ylmethyl)-2,3-dihydro-1H-benzimidazole-5-sulfonic acid (4-ethylphenyl)isobutylamide (80 mg; 26%) is obtained in the form of an off-white crystalline solid.

$^1$H NMR (DMSO-d6) δ: 0.85 (dd, J=6.6, 1.3 Hz, 6H), 1.18 (t, J=7.6 Hz, 3H), 1.40 (dt, J=13.5, 6.7 Hz, 1H), 2.60 (q, J=7.6 Hz, 2H), 3.27 (d, J=7.3 Hz, 2H), 4.19 (dd, J=15.2, 3.5 Hz, 1H), 4.30 (dd, J=15.2, 6.9 Hz, 1H), 4.37 (dd, J=8.6, 6.2 Hz, 1H), 4.64 (t, J=8.4 Hz, 1H), 5.10-5.19 (m, 1H), 6.93-6.99 (m, 2H), 7.02 (d, J=1.7 Hz, 1H), 7.15-7.22 (m, 2H), 7.27 (dd, J=8.4, 1.8 Hz, 1H), 7.40 (d, J=8.4 Hz, 1H), 11.29 (s, 1H).

MS: [M+H]=474

Example 7: Synthesis of 2-oxo-1-(2-oxooxazolidin-5-ylmethyl)-2,3-dihydro-1H-benzimidazole-5-sulfonic acid (4-ethylphenyl)isobutylamide Compound 9

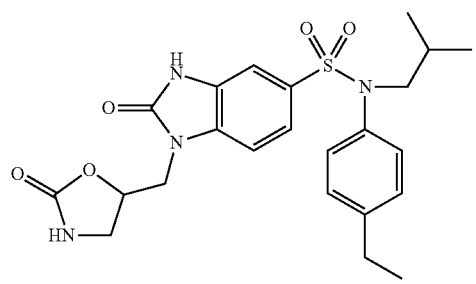

1. Synthesis of Intermediate 7.1

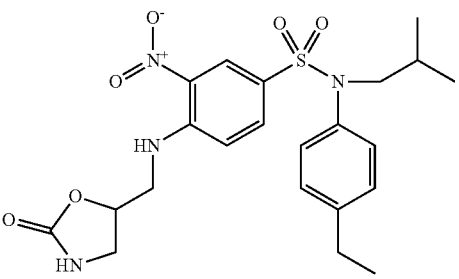 [SMILES: CCc1ccc(N(CC(C)C)S(=O)(=O)c2ccc(NCC3CNC(=O)O3)c([N+](=O)[O-])c2)cc1]

N-(4-ethylphenyl)-N-isobutyl-3-nitro-4-[(2-oxooxazolidin-5-ylmethyl)amino]benzenesulfonamide With a procedure similar to that described for intermediate 1.3, N-(4-ethylphenyl)-N-isobutyl-3-nitro-4-[(2-oxooxazolidin-5-ylmethyl)amino]benzenesulfonamide (240 mg; 100%) is obtained in the form of a yellow oil with a compliant $^1$H NMR.[2]

MS: [M+H]=477

2. Synthesis of Intermediate 7.2

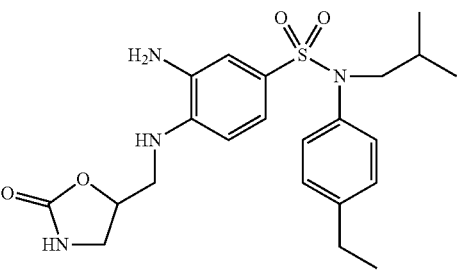 [SMILES: CCc1ccc(N(CC(C)C)S(=O)(=O)c2ccc(NCC3CNC(=O)O3)c(N)c2)cc1]

3-amino-N-(4-ethylphenyl)-N-isobutyl-4-[(2-oxooxazolidin-5-ylmethyl)amino]benzenesulfonamide With a procedure similar to that described for intermediate 1.4, 3-amino-N-(4-ethylphenyl)-N-isobutyl-4-[(2-oxooxazolidin-5-ylmethyl)amino]benzenesulfonamide (200 mg; 71%) is obtained in the form of a brown oil with a compliant $^1$H NMR.

MS: [M+H]=447

3. Synthesis of Compound 9 According to the Invention

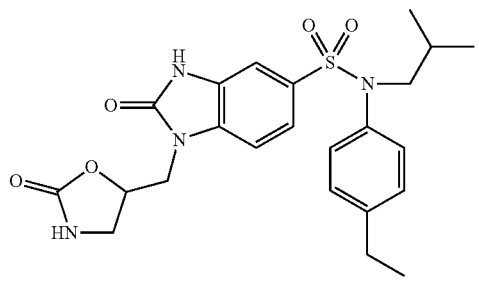 [SMILES: CCc1ccc(N(CC(C)C)S(=O)(=O)c2ccc3c(c2)[nH]c(=O)n3CC2CNC(=O)O2)cc1]

With a procedure similar to that described in example 1, 2-oxo-1-(2-oxooxazolidin-5-ylmethyl)-2,3-dihydro-1H-benzimidazole-5-sulfonic acid (4-ethylphenyl)isobutylamide (37 mg; 18%) is obtained in the form of a white crystalline solid.

1H NMR (DMSO-d6) δ: 0.85 (dd, J=6.7, 1.3 Hz, 6H), 1.18 (t, J=7.6 Hz, 3H), 1.34-1.47 (m, 1H), 2.61 (q, J=7.7 Hz, 2H), 3.27 (d, J=7.3 Hz, 2H), 3.36 (d, J=10.4 Hz, 2H), 3.61 (t, J=8.9 Hz, 1H), 4.07 (dd, J=14.9, 3.9 Hz, 1H), 4.16 (dd, J=15.0, 6.9 Hz, 1H), 6.92-7.00 (m, 2H), 7.01 (d, J=1.8 Hz, 1H), 7.19 (d, J=8.3 Hz, 2H), 7.26 (dd, J=8.3, 1.8 Hz, 1H), 7.37 (d, J=8.3 Hz, 1H), 7.56 (s, 1H), 11.25 (s, 1H).

MS: [M+H]=473

Example 8: Synthesis of 2-oxo-1-(2-oxotetrahydrofuran-3-ylmethyl)-2,3-dihydro-1H-benzimidazole-5-sulfonic acid (4-ethylphenyl)isobutylamide

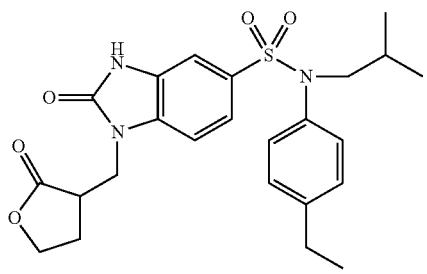 [SMILES: CCc1ccc(N(CC(C)C)S(=O)(=O)c2ccc3c(c2)[nH]c(=O)n3CC2CCOC2=O)cc1]

1. Synthesis of Intermediate 8.1

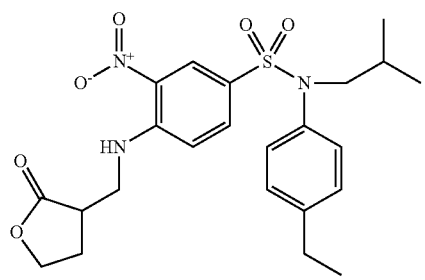 [SMILES: CCc1ccc(N(CC(C)C)S(=O)(=O)c2ccc(NCC3CCOC3=O)c([N+](=O)[O-])c2)cc1]

N-(4-ethylphenyl)-N-isobutyl-3-nitro-4-[(2-oxotetrahydrofuran-3-ylmethyl)amino]benzenesulfonamide With a procedure similar to that described for intermediate 1.3, N-(4-ethylphenyl)-N-isobutyl-3-nitro-4-[(2-oxotetrahydrofuran-3-ylmethyl)amino]benzenesulfonamide (290 mg; 97%) is obtained in the form of a brown oil with a compliant H NMR.

MS: [M+H]=476

2. Synthesis of Intermediate 8.2

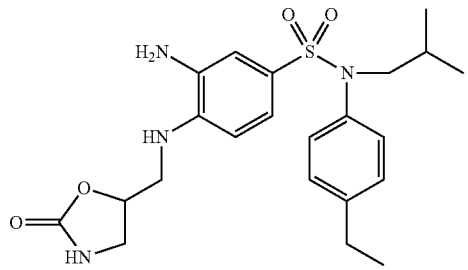 [SMILES: CCc1ccc(N(CC(C)C)S(=O)(=O)c2ccc(NCC3CNC(=O)O3)c(N)c2)cc1]

3-amino-N-(4-ethylphenyl)-N-isobutyl-4-[(2-oxotetrahydrofuran-3-ylmethyl)amino]benzenesulfonamide With a procedure similar to that described for intermediate 1.4, 3-amino-N-(4-ethylphenyl)-N-isobutyl-4-[(2-oxotetrahydrofuran-3-ylmethyl)amino]benzenesulfonamide (260 mg; 96%) is obtained in the form of a gray oil with a compliant 1H NMR.

MS: [M+H]=446

3. Synthesis of 2-oxo-1-(2-oxotetrahydrofuran-3-ylmethyl)-23-dihydro-1H-benzimidazole-5-sulfonic acid (4-ethylphenyl)isobutylamide

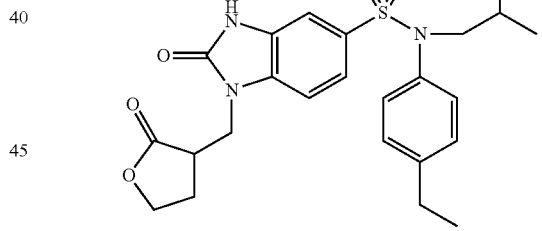

With a procedure similar to that described in example 1, 2-oxo-1-(2-oxotetrahydrofuran-3-ylmethyl)-2,3-dihydro-1H-benzimidazole-5-sulfonic acid (4-ethylphenyl)isobutylamide (145 mg; 52%) is obtained in the form of an off-white solid.

1H NMR (DMSO-d6) δ: 0.84 (d, J=6.6 Hz, 6H), 1.18 (t, J=7.6 Hz, 3H), 1.38 (tt, J=11.8, 5.8 Hz, 1H), 2.02-2.17 (m, 1H), 2.23 (dtt, J=9.2, 6.7, 3.3 Hz, 1H), 2.60 (q, J=7.6 Hz, 2H), 3.20 (ddt, J=10.4, 8.6, 4.2 Hz, 1H), 3.27 (d, J=7.3 Hz, 2H), 4.07 (dd, J=14.5, 8.3 Hz, 1H), 4.12-4.20 (m, 2H), 4.33 (td, J=8.5, 2.8 Hz, 1H), 6.93-7.00 (m, 2H), 7.01 (d, J=1.7 Hz, 1H), 7.14-7.22 (m, 2H), 7.26 (dd, J=8.3, 1.8 Hz, 1H), 7.37 (d, J=8.3 Hz, 1H), 11.23 (s, 1H).

MS: [M+H]=472

Example 9: Synthesis of 2-oxo-1-pyridin-4-ylmethyl-2,3-dihydro-1H-benzimidazole-5-sulfonic acid (4-ethylphenyl)isobutylamide

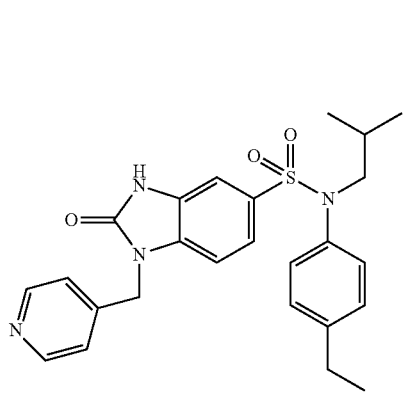

Compound 10

1. Synthesis of Intermediate 9.1

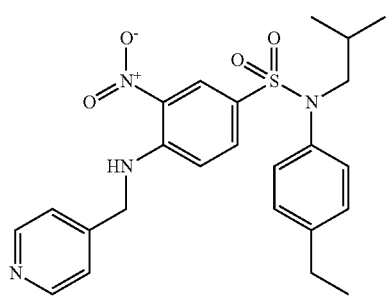 [SMILES: CCc1ccc(N(CC(C)C)S(=O)(=O)c2ccc(NCc3ccncc3)c([N+](=O)[O-])c2)cc1]

N-(4-ethylphenyl)-N-isobutyl-3-nitro-4-[(pyridin-4-ylmethyl)amino]benzenesulfonamide A mixture of 4-chloro-N-(4-ethylphenyl)-N-isobutyl-3-nitrobenzenesulfonamide (500 mg; 1.26 mmol), tetrahydrofuran (10 ml), cesium carbonate (516 mg; 1.89 mmol) and 4-picolylamine (409 mg; 3.78 mmol) is stirred for 5 hours at a temperature of 60° C., diluted with ethyl acetate (20 ml).

The organic phase is washed with saturated NH$_4$Cl solution (20 ml), with saturated NaHCO$_3$ solution (20 ml) and with water (20 ml), dried (MgSO$_4$), filtered and concentrated to dryness.

The crude product is chromatographed on silica gel (eluent: heptane/ethyl acetate, from 0 to 100% of ethyl acetate). The N-(4-ethylphenyl)-N-isobutyl-3-nitro-4-[(pyridin-4-ylmethyl)amino]benzenesulfonamide (520 mg; 92%) is obtained in the form of a yellow solid with a compliant $^1$H NMR.

MS: [M+H]=469

2. Synthesis of Intermediate 9.2

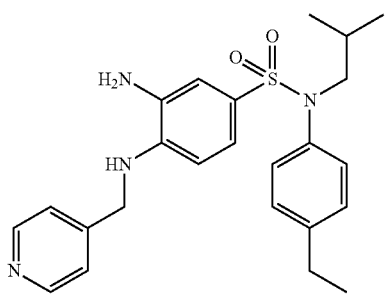 [SMILES: CCc1ccc(N(CC(C)C)S(=O)(=O)c2ccc(NCc3ccncc3)c(N)c2)cc1]

3-amino-N-(4-ethylphenyl)-N-isobutyl-4-[(pyridin-4-ylmethyl)amino]benzenesulfonamide Platinum(IV) oxide (7.27 mg; 0.03 mmol) is added to a solution, degassed under argon, of N-(4-ethylphenyl)-N-isobutyl-3-nitro-4-[(pyridin-4-ylmethyl)amino]benzenesulfonamide (150 mg; 0.32 mmol) in methanol (5 ml). The reaction medium is placed under 1 atmosphere of hydrogen and stirred for 1 hour, filtered through Celite and concentrated to dryness.

The 3-amino-N-(4-ethylphenyl)-N-isobutyl-4-[(oxetan-3-ylmethyl)amino]benzenesulfonamide (140 mg; 100%) is obtained in the form of an oil with a compliant $^1$H NMR.

MS: [M−H]=437

3. Synthesis of Compound 10 (Compound 275) According to the Invention

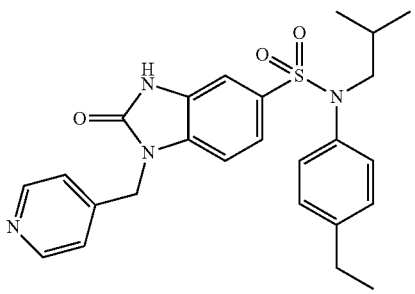 [SMILES: CCc1ccc(N(CC(C)C)S(=O)(=O)c2ccc3c(c2)[nH]c(=O)n3Cc2ccncc2)cc1]

With a procedure similar to that described for example 1, 2-oxo-1-pyridin-4-ylmethyl-2,3-dihydro-1H-benzimidazole-5-sulfonic acid (4-ethylphenyl)isobutylamide (70 mg; 44%) is obtained in the form of a white solid.

$^1$H NMR (DMSO-d6) δ: 0.83 (d, J=6.6 Hz, 6H), 1.18 (t, J=7.6 Hz, 3H), 2.55-2.64 (m, 3H), 3.26 (d, J=7.3 Hz, 2H), 5.12 (s, 2H), 6.91-6.99 (m, 2H), 7.06 (d, J=1.4 Hz, 1H), 7.14-7.19 (m, 2H), 7.20-7.23 (m, 2H), 7.25-7.28 (m, 2H), 8.51-8.56 (m, 2H), 11.36 (s, 1H).

MS: [M−H]=463

Example 10: Synthesis of 2-oxo-1-(tetrahydropyran-4-yl)-2,3-dihydro-1H-benzimidazole-5-sulfonic acid (4-ethylphenyl)isobutylamide

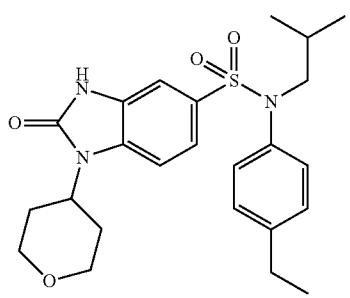

Compound 11

1. Synthesis of Intermediate 10.1

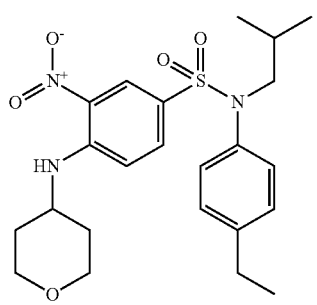 [SMILES: CCc1ccc(N(CC(C)C)S(=O)(=O)c2ccc(NC3CCOCC3)c([N+](=O)[O-])c2)cc1]

N-(4-ethylphenyl)-N-isobutyl-3-nitro-4-(tetrahydropyran-4-ylamino)benzenesulfonamide With a procedure similar to that described for intermediate 1.3, N-(4-ethylphenyl)-N-isobutyl-3-nitro-4-(tetrahydropyran-4-ylamino)benzenesulfonamide (215 mg; 92%) is obtained in the form of a yellow oil with a compliant $^1$H NMR.[2]

MS: [M+H]=462

2. Synthesis of Intermediate 10.2

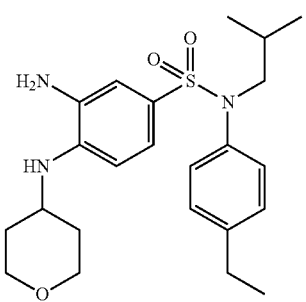 [SMILES: CCc1ccc(N(CC(C)C)S(=O)(=O)c2ccc(NC3CCOCC3)c(N)c2)cc1]

3-amino-N-(4-ethylphenyl)-N-isobutyl-4-(tetrahydropyran-4-ylamino)benzenesulfonamide With a procedure similar to that described for intermediate 1.4, 3-amino-N-(4-ethylphenyl)-N-isobutyl-4-(tetrahydropyran-4-ylamino)benzenesulfonamide (195 mg; 97%) is obtained in the form of a brown oil with a compliant $^1$H NMR.

MS: [M+H]=432

3. Synthesis of Compound 11 According to the Invention

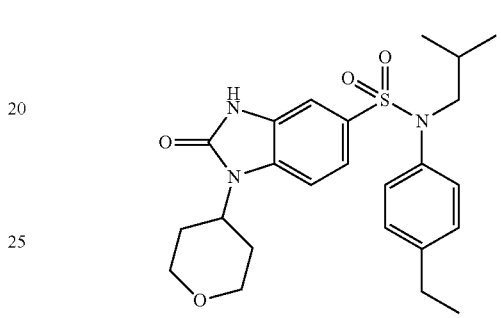

With a procedure similar to that described in example 1, 2-oxo-1-(tetrahydropyran-4-yl)-2,3-dihydro-1H-benzimidazole-5-sulfonic acid (4-ethylphenyl)isobutylamide (37 mg; 18%) is obtained in the form of an off-white crystalline solid.

$^1$H NMR (DMSO-d6) δ: 0.84 (d, J=6.6 Hz, 6H), 1.19 (t, J=7.6 Hz, 3H), 1.39 (dq, J=13.4, 6.7 Hz, 1H), 1.67 (d, J=11.5 Hz, 2H), 2.30-2.45 (m, 2H), 2.61 (q, J=7.6 Hz, 2H), 3.26 (d, J=7.3 Hz, 2H), 3.48 (dd, J=12.6, 10.6 Hz, 2H), 3.94-4.05 (m, 2H), 4.40-4.52 (m, 1H), 6.99 (d, J=8.4 Hz, 2H), 7.02 (d, J=1.8 Hz, 1H), 7.15-7.23 (m, 2H), 7.22 (dd, J=8.4, 1.8 Hz, 1H), 7.45 (d, J=8.5 Hz, 1H), 11.16 (s, 1H).

MS: [M+H]=458

Example 11: Synthesis of tert-butyl 4-{5-[(4-ethylphenyl)isobutylsulfamoyl]-2-oxo-2,3-dihydrobenzimidazol-1-yl}piperidine-1-carboxylate

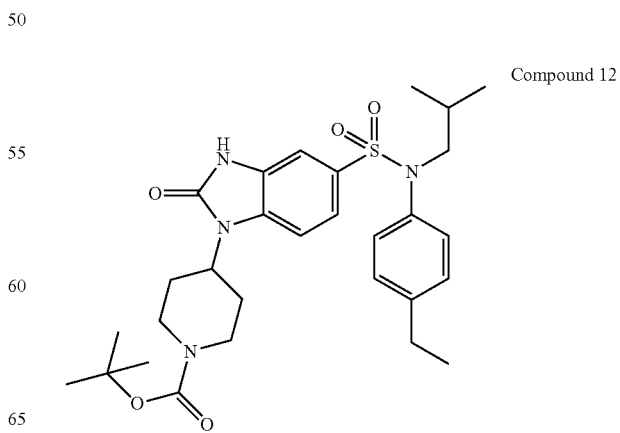

Compound 12

1. Synthesis of Intermediate 11.1

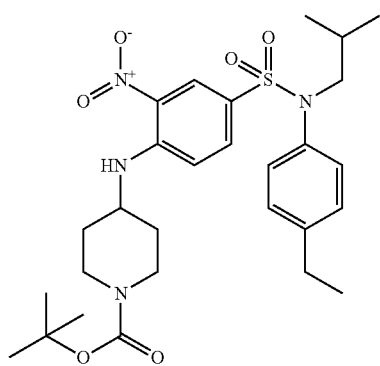 [SMILES: CCc1ccc(N(CC(C)C)S(=O)(=O)c2ccc(NC3CCN(C(=O)OC(C)(C)C)CC3)c([N+](=O)[O-])c2)cc1]

tert-butyl 4-{4-[(4-ethylphenyl)isobutylsulfamoyl]-2-nitro-phenylamino}piperidine-1-carboxylate With a procedure similar to that described for intermediate 1.3, tert-butyl 4-{4-[(4-ethylphenyl)isobutylsulfamoyl]-2-nitro-phenylamino}piperidine-1-carboxylate (353 mg; 100%) is obtained in the form of a brown oil with a compliant H NMR.

MS: [M+H]=461

2. Synthesis of Intermediate 11.2

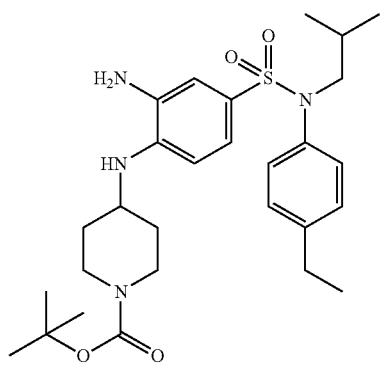 [SMILES: CCc1ccc(N(CC(C)C)S(=O)(=O)c2ccc(NC3CCN(C(=O)OC(C)(C)C)CC3)c(N)c2)cc1]

tert-butyl 4-{2-amino-4-[(4-ethylphenyl)isobutylsulfamoyl]phenylamino}piperidine-1-carboxylate With a procedure similar to that described for intermediate 1.4, tert-butyl 4-{2-amino-4-[(4-ethylphenyl)isobutylsulfamoyl]phenylamino}piperidine-1-carboxylate (340 mg; 100%) is obtained in the form of a brown oil with a compliant $^1$H NMR.

MS: [M+H]=531

3. Synthesis of Compound 12 According to the Invention

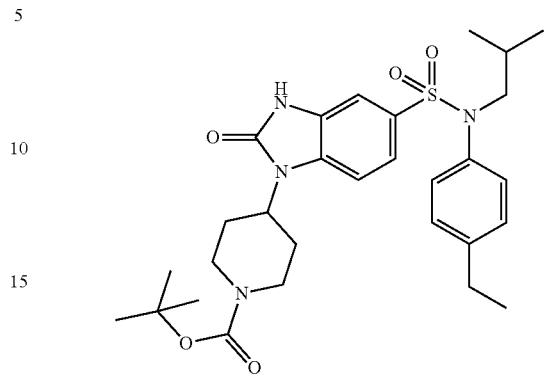

With a procedure similar to that described in example 1, tert-butyl 4-{5-[(4-ethylphenyl)isobutylsulfamoyl]-2-oxo-2,3-dihydrobenzimidazol-1-yl}piperidine-1-carboxylate (80 mg; 22%) is obtained in the form of a beige-colored crystalline solid.

$^1$H NMR (DMSO-d6) δ: 0.84 (d, J=6.6 Hz, 6H), 1.19 (t, J=7.6 Hz, 3H), 1.39 (dd, J=13.6, 6.9 Hz, 1H), 1.44 (s, 9H), 1.72 (d, J=12.4 Hz, 2H), 2.13-2.27 (m, 2H), 2.61 (q, J=7.6 Hz, 2H), 2.88 (s, 2H), 3.25 (d, J=7.4 Hz, 2H), 4.11 (s, 2H), 4.39 (t, J=12.4 Hz, 1H), 6.98 (d, J=8.4 Hz, 2H), 7.02 (d, J=1.9 Hz, 1H), 7.17-7.22 (m, 3H), 7.40 (d, J=8.5 Hz, 1H), 11.18 (s, 1H).

MS: [M+H]=557

Example 12: Synthesis of 2-oxo-1-piperidin-4-yl-2,3-dihydro-1H-benzimidazole-5-sulfonic acid (4-ethylphenyl)isobutylamide Compound 13

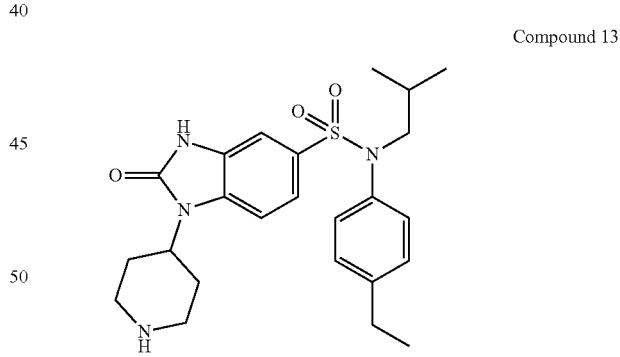

A mixture of tert-butyl 4-{5-[(4-ethylphenyl)isobutylsulfamoyl]-2-oxo-2,3-dihydrobenzimidazol-1-yl}piperidine-1-carboxylate (85.0 mg; 0.15 mmol) in dichloromethane (2 ml) and trifluoroacetic acid (175.4 µl; 2.29 mmol) is stirred overnight at room temperature and the medium is then concentrated under vacuum. The 2-oxo-1-piperidin-4-yl-2,3-dihydro-1H-benzimidazole-5-sulfonic acid (4-ethylphenyl)isobutylamide (80 mg; 26%) is obtained in the form of an off-white crystalline solid.

$^1$H NMR (DMSO-d6) δ: 0.85 (d, J=6.7 Hz, 6H), 1.14-1.23 (m, 3H), 1.41 (p, J=6.8 Hz, 1H), 1.92 (d, J=13.3 Hz, 2H), 2.61 (q, J=7.6 Hz, 2H), 3.10 (d, J=12.4 Hz, 2H), 3.26 (d, J=7.3 Hz, 2H), 3.45 (d, J=12.5 Hz, 2H), 4.57 (t, J=12.1 Hz,

1H), 6.95-7.03 (m, 2H), 7.06 (d, J=1.7 Hz, 1H), 7.16-7.23 (m, 2H), 7.26 (dd, J=8.4, 1.8 Hz, 1H), 7.42 (d, J=8.4 Hz, 1H), 8.59 (d, J=11.0 Hz, 1H), 11.24 (s, 1H).
MS: [M+H]=457

Example 13: Synthesis of 1-(1-methanesulfonylpiperidin-4-yl)-2-oxo-2,3-dihydro-1H-benzimidazole-5-sulfonic acid (4-ethylphenyl)isobutylamide

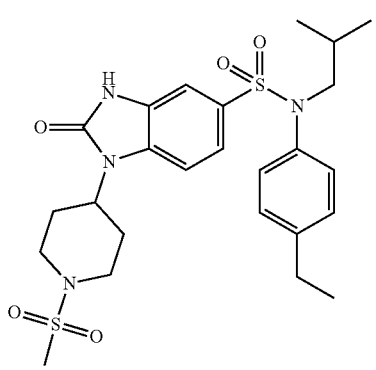

Compound 14

Methanesulfonyl chloride (15.26 µl; 0.20 mmol) and triethylamine (27.32 µl; 0.20 mmol) are added to a solution of 2-oxo-1-piperidin-4-yl-2,3-dihydro-1H-benzimidazole-5-sulfonic acid (4-ethylphenyl)isobutylamide (60.00 mg; 0.13 mmol) in dichloromethane (0.50 ml). The reaction medium is hydrolyzed, diluted with dichloromethane and extracted. The organic phases are washed with water, dried (MgSO$_4$) and concentrated under vacuum.

The crude product is purified by preparative HPLC (C18 column, eluent: acetonitrile in water/0.1% of formic acid).

After recrystallization from an acetone/water mixture, 1-(1-methanesulfonylpiperidin-4-yl)-2-oxo-2,3-dihydro-1H-benzimidazole-5-sulfonic acid (4-ethylphenyl)isobutylamide (10.00 mg; 14.11%) is obtained in the form of an off-white crystalline solid.

$^1$H 1H NMR (DMSO-d6) δ: 0.84 (d, J=6.5 Hz, 6H), 1.19 (t, J=7.6 Hz, 3H), 1.40 (dt, J=13.7, 7.0 Hz, 1H), 1.84 (d, J=12.2 Hz, 2H), 2.39 (dd, J=12.5, 4.0 Hz, 2H), 2.61 (q, J=7.6 Hz, 2H), 2.91 (d, J=12.6 Hz, 2H), 2.95 (s, 3H), 3.26 (d, J=7.3 Hz, 2H), 3.74 (d, J=11.8 Hz, 2H), 4.29-4.46 (m, 1H), 6.96-7.04 (m, 3H), 7.21 (dd, J=12.4, 8.5 Hz, 3H), 7.42 (d, J=8.4 Hz, 1H), 11.20 (s, 1H).
MS: [M+H]=535

With a procedure similar to that for intermediate 1.1, corresponding to a reductive amination between 1 equivalent of aldehyde and 1.15 equivalents of aniline in tetrahydrofuran in the presence of 1.45 equivalents of sodium triacetoxyborohydride, the anilines of the table below are obtained:

| Intermediate 15.1 | 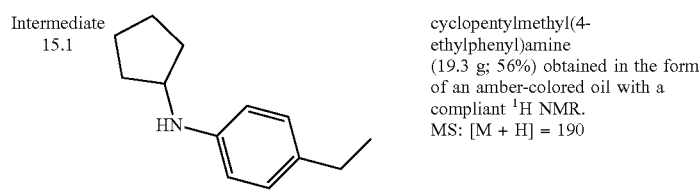 | cyclopentylmethyl(4-ethylphenyl)amine (19.3 g; 56%) obtained in the form of an amber-colored oil with a compliant $^1$H NMR. MS: [M + H] = 190 |
|---|---|---|
| Intermediate 16.1 | 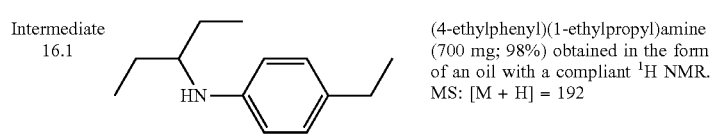 | (4-ethylphenyl)(1-ethylpropyl)amine (700 mg; 98%) obtained in the form of an oil with a compliant $^1$H NMR. MS: [M + H] = 192 |
| Intermediate 17.1 | 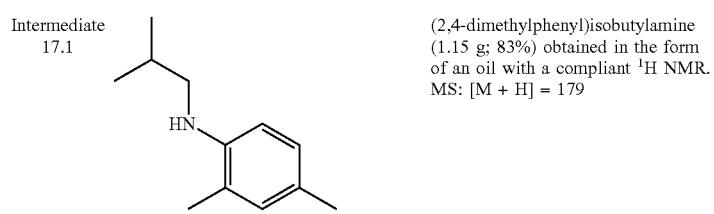 | (2,4-dimethylphenyl)isobutylamine (1.15 g; 83%) obtained in the form of an oil with a compliant $^1$H NMR. MS: [M + H] = 179 |
| Intermediate 19.1 | 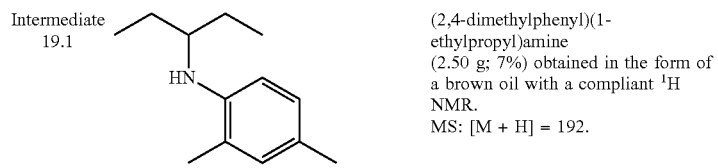 | (2,4-dimethylphenyl)(1-ethylpropyl)amine (2.50 g; 7%) obtained in the form of a brown oil with a compliant $^1$H NMR. MS: [M + H] = 192. |

Example 14: 2-oxo-1-(tetrahydropyran-4-ylmethyl)-2,3-dihydro-1H-benzimidazole-5-sulfonic acid (4-ethylphenyl)cyclopentylamide Compound 15

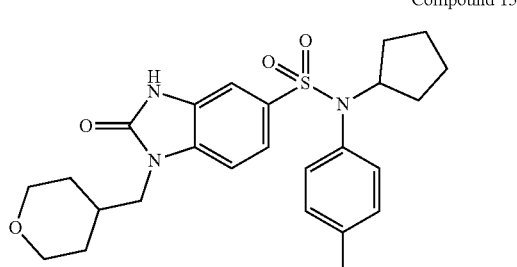

1. Synthesis of Intermediate 14.2

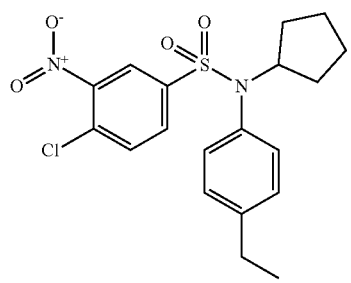 [SMILES: CCc1ccc(N(C2CCCC2)S(=O)(=O)c2ccc(Cl)c([N+](=O)[O-])c2)cc1]

4-chloro-N-(4-ethylphenyl)-N-cyclopentyl-3-nitrobenzenesulfonamide

With a procedure similar to that described for intermediate 1.2 applied to intermediate 14.1, 4-chloro-N-(4-ethylphenyl)-N-cyclopentyl-3-nitrobenzenesulfonamide (440 mg; 28%) is obtained in the form of an off-white solid with a compliant $^1$H NMR.

MS: [M+H]=409

2. Synthesis of Intermediate 14.3

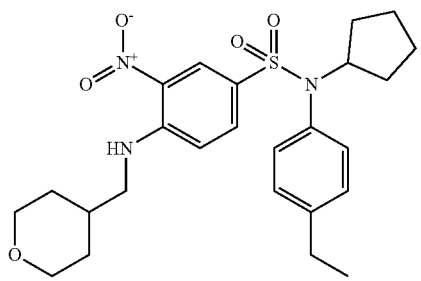 [SMILES: CCc1ccc(N(C2CCCC2)S(=O)(=O)c2ccc(NCC3CCOCC3)c([N+](=O)[O-])c2)cc1]

N-(4-ethylphenyl)-N-cyclopentyl-3-nitro-4-[(tetrahydropyran-4-ylmethyl)amino]benzenesulfonamide With a procedure similar to that described for intermediate 1.3, N-(4-ethylphenyl)-N-cyclopentyl-3-nitro-4-[(tetrahydropyran-4-ylmethyl)amino]benzenesulfonamide (480 mg; 91%) is obtained in the form of an orange-colored solid with a compliant $^1$H NMR.

MS: [M+H]=488

3. Synthesis of Intermediate 14.4

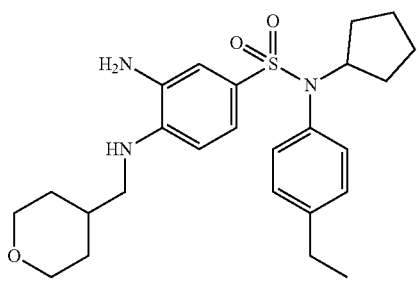 [SMILES: CCc1ccc(N(C2CCCC2)S(=O)(=O)c2ccc(NCC3CCOCC3)c(N)c2)cc1]

3-amino-N-(4-ethylphenyl)-N-cyclopentyl-4-[(tetrahydropyran-4-ylmethyl)amino]benzenesulfonamide With a procedure similar to that described for intermediate 1.4, 3-amino-N-(4-ethylphenyl)-N-cyclopentyl-4-[(tetrahydropyran-4-ylmethyl)amino]benzenesulfonamide (420 mg; 97%) is obtained in the form of a beige-colored solid with a compliant $^1$H NMR.

MS: [M+H]=458

4. Synthesis of Compound 15 (Compound 280) According to the Invention

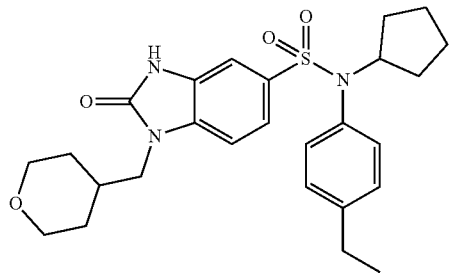 [SMILES: CCc1ccc(N(C2CCCC2)S(=O)(=O)c2ccc3c(c2)[nH]c(=O)n3CC2CCOCC2)cc1]

With a procedure similar to that described in example 1, 2-oxo-1-(tetrahydropyran-4-ylmethyl)-2,3-dihydro-1H-benzimidazole-5-sulfonic acid (4-ethylphenyl)cyclopentylamide (262 mg; 59%) is obtained in the form of a white crystalline solid after recrystallization from an acetone/water mixture.

$^1$H NMR (DMSO-d6) δ: 1.19 (t, J=7.6 Hz, 3H), 1.32 (tdd, J=12.9, 7.2, 4.5 Hz, 3H), 1.41 (dd, J=7.6, 4.7 Hz, 1H), 1.49 (d, J=11.8 Hz, 1H), 1.73 (dd, J=11.5, 6.5 Hz, 2H), 2.03 (ddd, J=11.3, 7.6, 4.0 Hz, 1H), 2.62 (q, J=7.6 Hz, 2H), 3.24 (td, J=11.6, 2.1 Hz, 2H), 3.74 (d, J=7.2 Hz, 2H), 3.80-3.87 (m, 2H), 4.43 (tt, J=9.3, 7.3 Hz, 1H), 6.88-6.91 (m, 2H), 7.19-7.21 (m, 2H), 7.21 (d, J=1.9 Hz, 1H), 7.35-7.43 (m, 2H), 11.19 (s, 1H)

MS: [M+H]=484

Example 15: Synthesis of 2-oxo-1-(tetrahydropyran-4-ylmethyl)-2,3-dihydro-1H-benzimidazole-5-sulfonic acid (4-ethylphenyl)(1-ethylpropyl)amide Compound 16

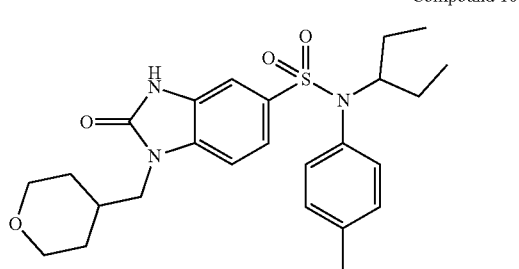

1. Synthesis of Intermediate 15.2

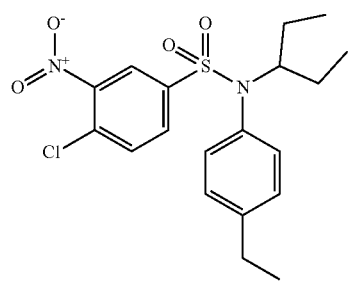 [SMILES: CCc1ccc(N(C(CC)CC)S(=O)(=O)c2ccc(Cl)c([N+](=O)[O-])c2)cc1]

4-chloro-N-(4-ethylphenyl)-N-(1-ethylpropyl)-3-nitrobenzenesulfonamide

With a procedure similar to that described for intermediate 1.2 applied to intermediate 15.1, 4-chloro-N-(4-ethylphenyl)-N-(1-ethylpropyl)-3-nitrobenzenesulfonamide (900 mg; 88%) is obtained in the form of an orange-colored oil with a compliant $^1$H NMR.

MS: [M+H]=411

2. Synthesis of Intermediate 15.3

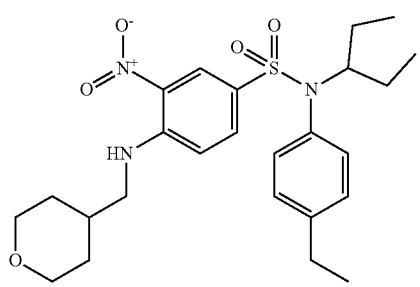 [SMILES: CCc1ccc(N(C(CC)CC)S(=O)(=O)c2ccc(NCC3CCOCC3)c([N+](=O)[O-])c2)cc1]

N-(4-ethylphenyl)-N-(1-ethylpropyl)-3-nitro-4-[(tetrahydropyran-4-ylmethyl)amino]benzenesulfonamide With a procedure similar to that described for intermediate 1.3, N-(4-ethylphenyl)-N-(1-ethylpropyl)-3-nitro-4-[(tetrahydropyran-4-ylmethyl)amino]benzenesulfonamide (1.07 g; 100%) is obtained in the form of an amber-colored oil with a compliant $^1$H NMR.

MS: [M+H]=490

3. Synthesis of Intermediate 15.4

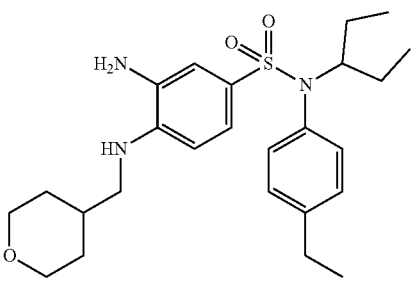

3-amino-N-(4-ethylphenyl)-N-(1-ethylpropyl)-4-[(tetrahydropyran-4-ylmethyl)amino]benzenesulfonamide By analogy with the procedure described for intermediate 1.3, 3-amino-N-(4-ethylphenyl)-N-(1-ethylpropyl)-4-[(tetrahydropyran-4-ylmethyl)amino]benzenesulfonamide (910 mg; 83%) is obtained in the form of an amber-colored oil with a compliant $^1$H NMR.

MS: [M+H]=460

4. Synthesis of Compound 16 According to the Invention

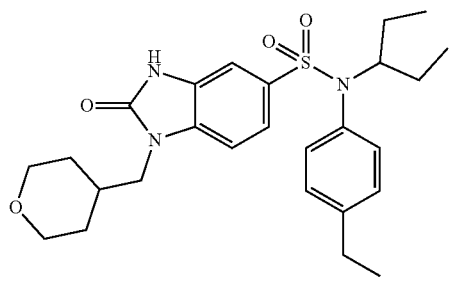 [SMILES: CCc1ccc(N(C(CC)CC)S(=O)(=O)c2ccc3c(c2)[nH]c(=O)n3CC2CCOCC2)cc1]

With a procedure similar to that described in example 1, 2-oxo-1-(tetrahydropyran-4-ylmethyl)-2,3-dihydro-1H-benzimidazole-5-sulfonic acid (4-ethylphenyl)(1-ethylpropyl) amide (120 mg; 12%) is obtained in the form of a white crystalline solid after recrystallization from an acetone/water mixture.

$^1$H NMR (DMSO-d6) δ: 0.87 (t, J=7.3 Hz, 6H), 1.08-1.16 (m, 2H), 1.19 (t, J=7.6 Hz, 3H), 1.29 (dddd, J=14.4, 12.7, 7.1, 4.9 Hz, 4H), 1.43-1.51 (m, 2H), 2.02 (ddt, J=11.5, 7.8, 3.8 Hz, 1H), 2.62 (q, J=7.6 Hz, 2H), 3.23 (td, J=11.6, 2.1 Hz, 2H), 3.74 (d, J=7.2 Hz, 2H), 3.79-3.86 (m, 2H), 3.88 (ddd, J=8.1, 5.7, 2.5 Hz, 1H), 6.88-6.92 (m, 2H), 7.16 (d, J=1.2 Hz, 1H), 7.19-7.24 (m, 2H), 7.35 (d, J=1.1 Hz, 2H), 11.19 (s, 1H)

MS: [M+H]=486

Example 16: Synthesis of 2-oxo-1-(tetrahydropyran-4-ylmethyl)-2,3-dihydro-1H-benzimidazole-5-sulfonic acid (2,4-dimethylphenyl)isobutylamide

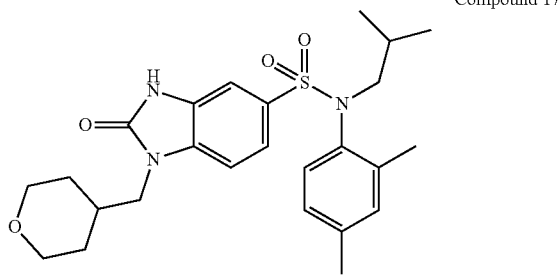

Compound 17

1. Synthesis of Intermediate 16.2

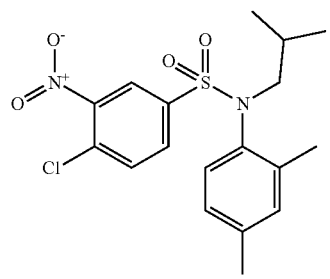 [SMILES: Cc1ccc(N(CC(C)C)S(=O)(=O)c2ccc(Cl)c([N+](=O)[O-])c2)c(C)c1]

4-chloro-N-(2,4-dimethylphenyl)-N-isobutyl-3-nitrobenzenesulfonamide

With a procedure similar to that described for intermediate 1.2 applied to intermediate 16.1, 4-chloro-N-(2,4-dimethylphenyl)-N-isobutyl-3-nitrobenzenesulfonamide (665 mg; 88%) is obtained in the form of a brown oil with a compliant ¹H NMR.
MS: [M−H]=396

2. Synthesis of Intermediate 16.3

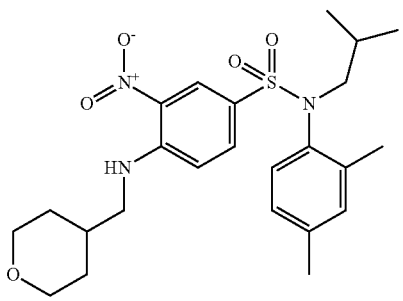 [SMILES: Cc1ccc(N(CC(C)C)S(=O)(=O)c2ccc(NCC3CCOCC3)c([N+](=O)[O-])c2)c(C)c1]

N-(2,4-dimethylphenyl)-N-isobutyl-3-nitro-4-[(tetrahydropyran-4-ylmethyl)amino]benzenesulfonamide With a procedure similar to that described for intermediate 1.3, N-(2,4-dimethylphenyl)-N-isobutyl-3-nitro-4-[(tetrahydropyran-4-ylmethyl)amino]benzenesulfonamide (740 mg; 93%) is obtained in the form of a brown oil with a compliant ¹H NMR.
MS: [M+H]=476

3. Synthesis of Intermediate 16.4

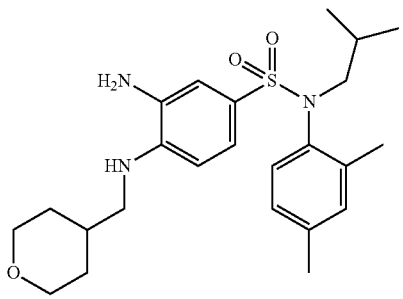 [SMILES: Cc1ccc(N(CC(C)C)S(=O)(=O)c2ccc(NCC3CCOCC3)c(N)c2)c(C)c1]

3-amino-N-(2,4-dimethylphenyl)-N-isobutyl-4-[(tetrahydropyran-4-ylmethyl)amino]benzenesulfonamide By analogy with the procedure described for intermediate 1.4, 3-amino-N-(2,4-dimethylphenyl)-N-isobutyl-4-[(tetrahydropyran-4-ylmethyl)amino]benzenesulfonamide (693 g; 100%) is obtained in the form of an amber-colored oil with a compliant ¹H NMR.
MS: [M+H]=446

4. Synthesis of Compound 17 According to the Invention

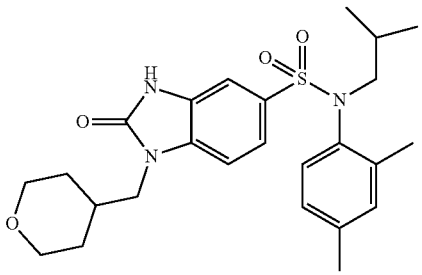 [SMILES: Cc1ccc(N(CC(C)C)S(=O)(=O)c2ccc3c(c2)[nH]c(=O)n3CC2CCOCC2)c(C)c1]

With a procedure similar to that described in example 1, 2-oxo-1-(tetrahydropyran-4-ylmethyl)-2,3-dihydro-1H-benzimidazole-5-sulfonic acid (2,4-dimethylphenyl)isobutylamide (273 mg; 37%) is obtained in the form of a white crystalline solid after recrystallization from an acetone/water mixture.
¹H NMR (DMSO-d6) δ: 0.75 (d, J=6.6 Hz, 3H), 0.94 (d, J=6.5 Hz, 3H), 1.30 (qd, J=12.1, 4.4 Hz, 2H), 1.40 (dtd, J=9.0, 6.8, 4.8 Hz, 1H), 1.48 (dd, J=13.6, 3.5 Hz, 2H), 2.03 (dtq, J=11.2, 7.4, 3.9 Hz, 1H), 2.25 (d, J=3.5 Hz, 6H), 3.04 (dd, J=13.0, 4.6 Hz, 1H), 3.19-3.29 (m, 2H), 3.36 (dd, J=13.0, 9.0 Hz, 1H), 3.75 (d, J=7.2 Hz, 2H), 3.83 (dq, J=11.6, 1.9 Hz, 2H), 6.52 (d, J=8.1 Hz, 1H), 6.90 (dd, J=8.1, 2.1 Hz, 1H), 7.09 (dd, J=11.3, 1.9 Hz, 2H), 7.29 (dd, J=8.3, 1.8 Hz, 1H), 7.38 (d, J=8.3 Hz, 1H), 11.21 (s, 1H)
MS: [M+H]=472

Example 17: Synthesis of 2-oxo-1-(tetrahydropyran-4-ylmethyl)-2,3-dihydro-1H-benzimidazole-5-sulfonic acid cyclopentyl(2,4-dimethylphenyl)amide Compound 18

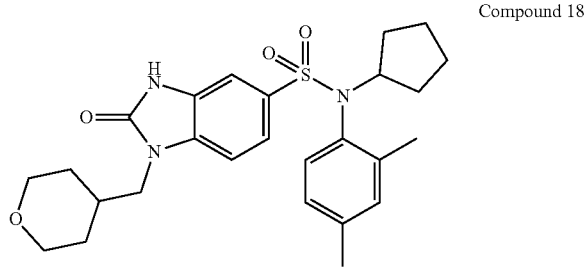 [SMILES: Cc1ccc(N(C2CCCC2)S(=O)(=O)c2ccc3c(c2)[nH]c(=O)n3CC2CCOCC2)c(C)c1]

1. Synthesis of Intermediate 17.1

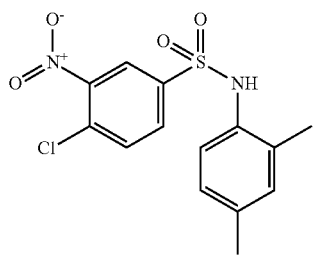 [SMILES: Cc1ccc(NS(=O)(=O)c2ccc(Cl)c([N+](=O)[O-])c2)c(C)c1]

4-chloro-N-(2,4-dimethylphenyl)-3-nitrobenzenesulfonamide

With a procedure similar to that described for intermediate 1.2, 4-chloro-N-(2,4-dimethylphenyl)-3-nitrobenzenesulfonamide (180 mg; 28%) is obtained in the form of a brown oil with a compliant ¹H NMR.

MS: [M−H]=339

2. Synthesis of Intermediate 17.2

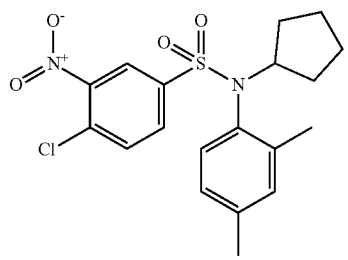 [SMILES: Cc1ccc(N(C2CCCC2)S(=O)(=O)c2ccc(Cl)c([N+](=O)[O-])c2)c(C)c1]

4-chloro-N-cyclopentyl-N-(2,4-dimethylphenyl)-3-nitrobenzenesulfonamide

A mixture of 4-chloro-N-(2,4-dimethylphenyl)-3-nitrobenzenesulfonamide (180 mg; 0.53 mmol), cesium carbonate (258 mg; 0.79 mmol) and iodocyclopentane (90 μl; 0.79 mmol) in 1-methyl-2-pyrrolidone (5 ml) is stirred overnight at a temperature of 80° C., hydrolyzed, diluted and extracted with acetate. The organic phases are combined, washed with water, dried (MgSO₄), filtered and concentrated under vacuum.

The 4-chloro-N-cyclopentyl-N-(2,4-dimethylphenyl)-3-nitrobenzenesulfonamide (216 mg; 100%) is obtained in the form of a brown oil with a compliant ¹H NMR.

3. Synthesis of Intermediate 17.3

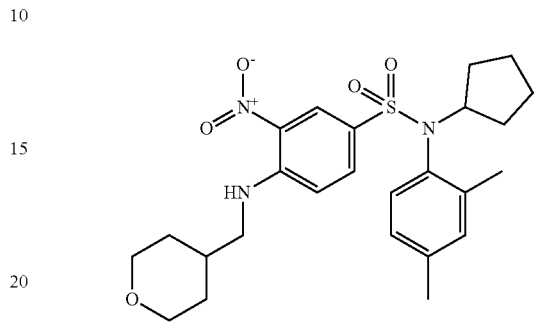

N-cyclopentyl-N-(2,4-dimethylphenyl)-3-nitro-4-[(tetrahydropyran-4-ylmethyl)amino]benzenesulfonamide With a procedure similar to that described for intermediate 1.3, N-cyclopentyl-N-(2,4-dimethylphenyl)-3-nitro-4-[(tetrahydropyran-4-ylmethyl)amino]benzenesulfonamide (105 mg; 35%) is obtained in the form of a yellow oil with a compliant ¹H NMR.

MS: [M+H]=488

4. Synthesis of Intermediate 17.4

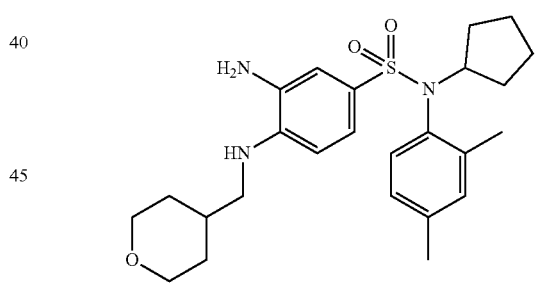

3-amino-N-cyclopentyl-N-(2,4-dimethylphenyl)-4-[(tetrahydropyran-4-ylmethyl)amino]benzenesulfonamide By analogy with the procedure described for intermediate 1.4, 3-amino-N-cyclopentyl-N-(2,4-dimethylphenyl)-4-[(tetrahydropyran-4-ylmethyl)amino]benzenesulfonamide (94 g; 100%) is obtained in the form of a greenish oil with a compliant ¹H NMR.

MS: [M+H]=458

5. Synthesis of Compound 18 According to the Invention

With a procedure similar to that described in example 1, 2-oxo-1-(tetrahydropyran-4-ylmethyl)-2,3-dihydro-1H-benzimidazole-5-sulfonic acid cyclopentyl(2,4-dimethylphenyl)amide (10 mg; 8%) is obtained in the form of a brown oil.

¹H NMR (CDCl₃-d) δ: 1.24 (d, J=11.7 Hz, 4H), 1.43 (dd, J=13.9, 7.6 Hz, 8H), 1.95-2.05 (m, 1H), 2.31 (s, 6H), 3.32-3.41 (m, 2H), 3.79 (d, J=7.2 Hz, 2H), 3.99 (dd, J=11.6, 4.1 Hz, 2H), 4.48 (ddd, J=10.1, 7.1, 3.0 Hz, 1H), 6.57 (d, J=8.0 Hz, 1H), 6.86 (d, J=8.2 Hz, 1H), 7.03 (d, J=8.4 Hz, 1H), 7.11 (d, J=2.1 Hz, 1H), 7.44 (d, J=1.7 Hz, 1H), 7.54 (dd, J=8.3, 1.7 Hz, 1H), 8.60 (s, 1H)

MS: [M+H]=484

Example 18: Synthesis of 2-oxo-1-(tetrahydropyran-4-ylmethyl)-2,3-dihydro-1H-benzimidazole-5-sulfonic acid (2,4-dimethylphenyl)(1-ethylpropyl) amide Compound 19

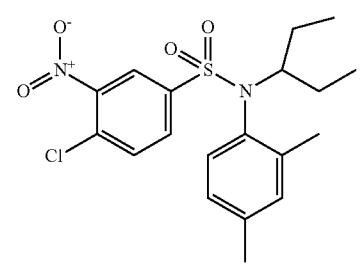 [SMILES: CCC(CC)N(c1ccc(C)cc1C)S(=O)(=O)c1ccc(Cl)c([N+](=O)[O-])c1]

1. Synthesis of Intermediate 18.2

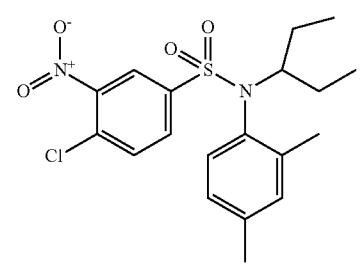 [SMILES: CCC(CC)N(c1ccc(C)cc1C)S(=O)(=O)c1ccc(Cl)c([N+](=O)[O-])c1]

4-chloro-N-(2,4-dimethylphenyl)-N-(1-ethylpropyl)-3-nitrobenzenesulfonamide

A mixture of 4-chloro-N-(2,4-dimethylphenyl)-3-nitrobenzenesulfonamide (480 mg; 1.41 mmol), cesium carbonate (138 mg; 4.23 mmol) and 3-bromopentane (520 µl; 4.23 mmol) in 1-methyl-2-pyrrolidone (5 ml) is stirred overnight at a temperature of 80° C., hydrolyzed and extracted with ethyl acetate. The organic phases are combined, washed with water, dried (MgSO₄), filtered and concentrated. The 4-chloro-N-(2,4-dimethylphenyl)-N-(1-ethylpropyl)-3-nitrobenzenesulfonamide (580 mg; 100%) is obtained in the form of a brown oil with a compliant ¹H NMR.

MS: [M+H]=411

2. Synthesis of Intermediate 18.3

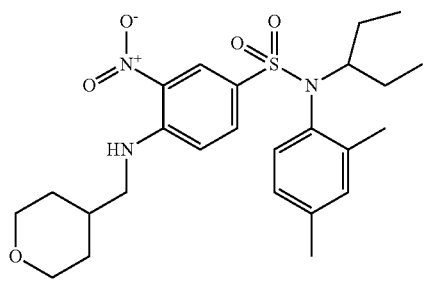 [SMILES: CCC(CC)N(c1ccc(C)cc1C)S(=O)(=O)c1ccc(NCC2CCOCC2)c([N+](=O)[O-])c1]

N-(2,4-dimethylphenyl)-N-(1-ethylpropyl)-3-nitro-4-[(tetrahydropyran-4-ylmethyl)amino]benzenesulfonamide With a procedure similar to that described for intermediate 1.3, N-(2,4-dimethylphenyl)-N-(1-ethylpropyl)-3-nitro-4-[(tetrahydropyran-4-ylmethyl)amino]benzenesulfonamide (450 mg; 41%) is obtained in the form of a brown oil with a compliant ¹H NMR.

MS: [M+H]=490

3. Synthesis of Intermediate 18.4

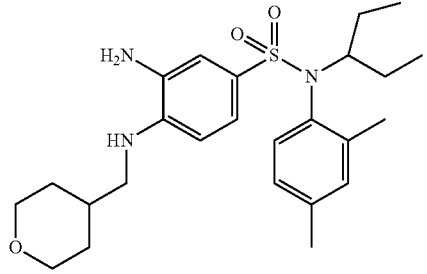 [SMILES: CCC(CC)N(c1ccc(C)cc1C)S(=O)(=O)c1ccc(NCC2CCOCC2)c(N)c1]

3-amino-N-(2,4-dimethylphenyl)-N-(1-ethylpropyl)-4-[(tetrahydropyran-4-ylmethyl)amino]benzenesulfonamide By analogy with the procedure described for intermediate 1.4, 3-amino-N-(2,4-dimethylphenyl)-N-(1-ethylpropyl)-4-[(tetrahydropyran-4-ylmethyl)amino]benzenesulfonamide (420 mg; 100%) is obtained in the form of an amber-colored oil with a compliant ¹H NMR.

MS: [M+H]=460

4. Synthesis of Compound 19 According to the Invention

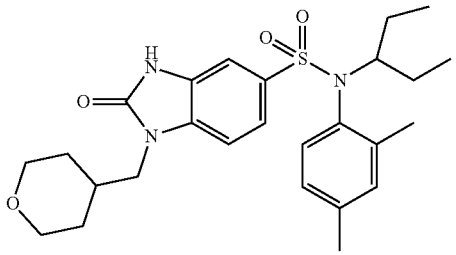 [SMILES: CCC(CC)N(c1ccc(C)cc1C)S(=O)(=O)c1ccc2c(c1)[nH]c(=O)n2CC1CCOCC1]

With a procedure similar to that described in example 1, 2-oxo-1-(tetrahydropyran-4-ylmethyl)-2,3-dihydro-1H-benzimidazole-5-sulfonic acid (2,4-dimethylphenyl)(1-ethylpropyl)amide (92 mg; 19%) is obtained in the form of an off-white crystalline solid after recrystallization from an acetone/water mixture.

$^1$H NMR (DMSO-d6) δ: 0.67 (t, J=7.3 Hz, 3H), 0.95 (t, J=7.3 Hz, 3H), 1.08-1.21 (m, 2H), 1.30 (ttd, J=14.6, 7.1, 3.9 Hz, 4H), 1.46 (d, J=13.3 Hz, 3H), 2.03 (ddd, J=11.4, 7.3, 3.8 Hz, 1H), 2.09 (s, OH), 2.24 (s, 3H), 2.28 (s, 3H), 3.23 (td, J=11.6, 2.2 Hz, 2H), 3.75 (d, J=7.3 Hz, 2H), 3.79-3.87 (m, 2H), 6.65 (d, J=8.1 Hz, 1H), 6.94 (dd, J=8.1, 2.2 Hz, 1H), 7.12-7.19 (m, 2H), 7.38 (d, J=1.6 Hz, 2H), 11.21 (s, 1H).

MS: [M+H]=486

Example 19: Synthesis of 1-(1,1-dioxohexahydro-1λ$^6$-thiopyran-4-ylmethyl)-2-oxo-2,3-dihydro-1H-benzimidazole-5-sulfonic acid (4-ethylphenyl)isobutylamide Compound 20

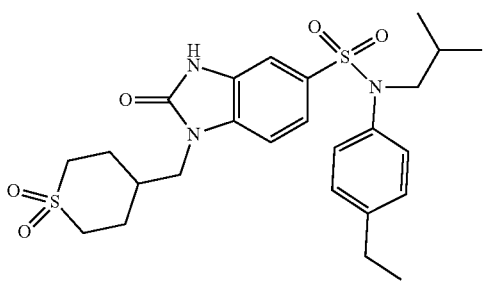

1. Synthesis of Intermediate 19.1

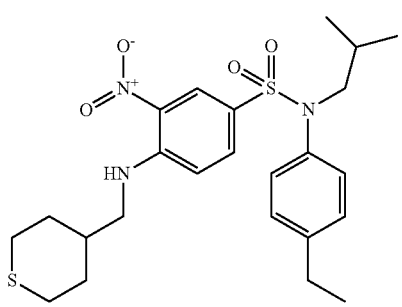 [SMILES: CCc1ccc(N(CC(C)C)S(=O)(=O)c2ccc(NCC3CCSCC3)c([N+](=O)[O-])c2)cc1]

N-(4-ethylphenyl)-N-isobutyl-3-nitro-4-[(tetrahydrothiopyran-4-ylmethyl)amino]benzenesulfonamide With a procedure similar to that described for intermediate 1.3, N-(4-ethylphenyl)-N-isobutyl-3-nitro-4-[(tetrahydrothiopyran-4-ylmethyl)amino]benzenesulfonamide (600 mg; 97%) is obtained in the form of a brown oil with a compliant $^1$H NMR.

MS: [M+H]=492

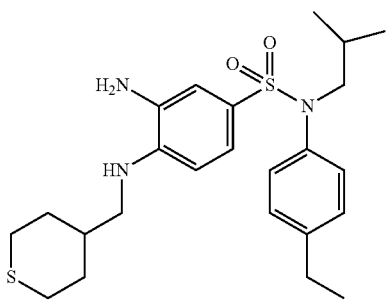 [SMILES: CCc1ccc(N(CC(C)C)S(=O)(=O)c2ccc(NCC3CCSCC3)c(N)c2)cc1]

3-amino-N-(4-ethylphenyl)-N-isobutyl-4-[(tetrahydrothiopyran-4-ylmethyl)amino]benzenesulfonamide By analogy with the procedure described for intermediate 1.4, 3-amino-N-(4-ethylphenyl)-N-isobutyl-4-[(tetrahydrothiopyran-4-ylmethyl)amino]benzenesulfonamide (543 mg; 96%) is obtained in the form of an amber-colored oil with a compliant $^1$H NMR.

MS: [M+H]=462

2. Synthesis of Compound 20 According to the Invention

With a procedure similar to that described in example 1, 1-(1,1-dioxohexahydro-λ$^6$-thiopyran-4-ylmethyl)-2-oxo-2,3-dihydro-1H-benzimidazole-5-sulfonic acid (4-ethylphenyl)isobutylamide (140 mg; 40%) is obtained in the form of a white crystalline solid after recrystallization from an acetone/water mixture.

$^1$H NMR (DMSO-d6) δ: 0.84 (d, J=6.6 Hz, 6H), 1.14-1.23 (m, 3H), 1.40 (dt, J=13.5, 6.8 Hz, 1H), 1.73 (q, J=12.4 Hz, 2H), 1.95 (d, J=13.8 Hz, 2H), 2.07-2.18 m, 1H), 2.61 (q, J=7.6 Hz, 2H), 3.00-3.17 (m, 4H), 3.27 (d, J=7.3 Hz, 2H), 3.80 (d, J=7.2 Hz, 2H), 6.97 (d, J=8.3 Hz, 2H), 7.02 (d, J=1.8 Hz, 1H), 7.14-7.22 (m, 2H), 7.24 (dd, J=8.4, 1.8 Hz, 1H), 7.39 (d, J=8.3 Hz, 1H), 11.17 (s, 1H).

MS: [M+H]=520

Part II: Synthesis of the Bicyclic Sulfonamides Via Reaction Scheme 2

Reaction scheme 2

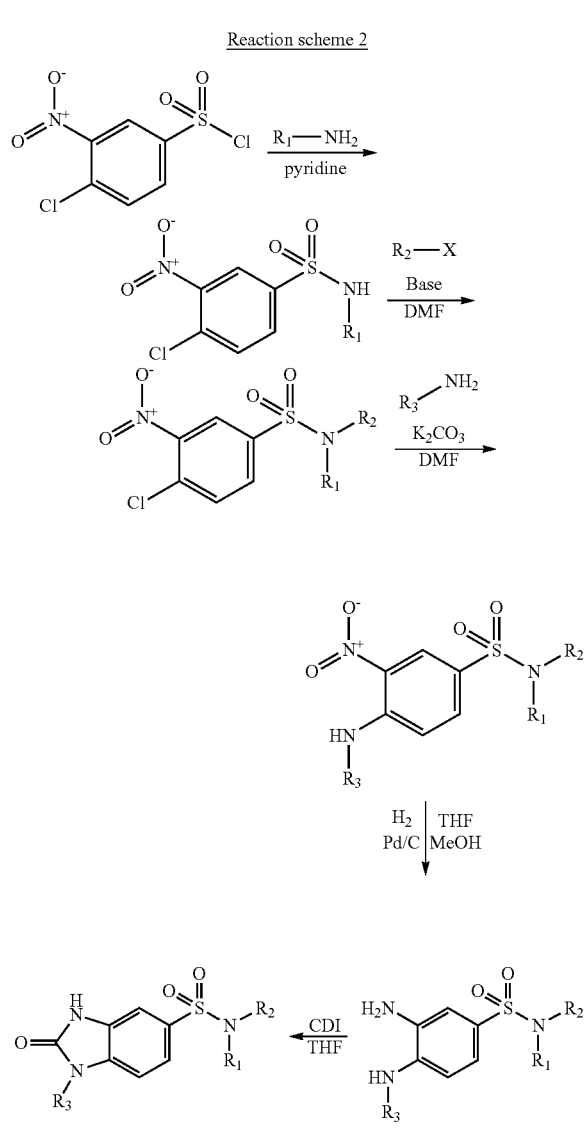

Example 21: Synthesis of 1-oxetan-3-ylmethyl-2-oxo-2,3-dihydro-1H-benzimidazole-5-sulfonic acid (4,6-dimethylpyridin-3-yl)isobutylamide

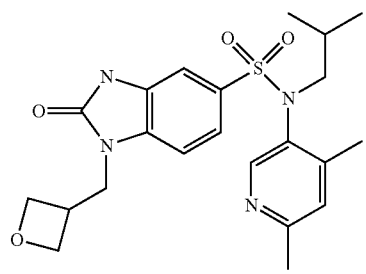 [SMILES: Cc1cc(C)c(N(CC(C)C)S(=O)(=O)c2ccc3c(c2)[nH]c(=O)n3CC2COC2)cn1]

1. Synthesis of Intermediate 21.1

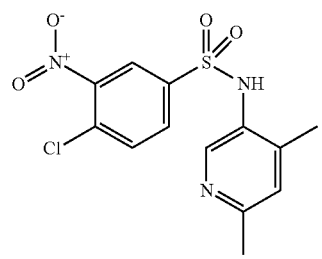 [SMILES: Cc1cc(C)c(NS(=O)(=O)c2ccc(Cl)c([N+](=O)[O-])c2)cn1]

4-chloro-N-(4,6-dimethylpyridin-3-yl)-3-nitrobenzenesulfonamide

4-Chloro-3-nitrobenzenesulfonyl chloride (500 mg; 1.91 mmol) is added to 4,6-dimethylpyridin-3-ylamine (487 mg; 3.83 mmol), triethylamine (53 μl; 0.38 mmol) and pyridine (5.2 ml). The reaction medium is stirred for 10 minutes at room temperature, hydrolyzed with saturated NH₄Cl solution and extracted with ethyl acetate. The organic phase is concentrated and then coevaporated with toluene.

The crude product is purified by preparative HPLC (C18 column, eluent: acetonitrile in water/0.1% of formic acid).

The 4-chloro-N-(4,6-dimethylpyridin-3-yl)-3-nitrobenzenesulfonamide (303 mg; 46%) is obtained in the form of a cream-colored solid with a compliant $^1$H NMR.

MS: [M−H]=340

2. Synthesis of Intermediate 21.2

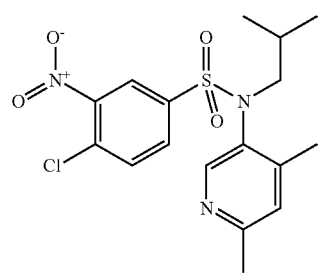 [SMILES: Cc1cc(C)c(N(CC(C)C)S(=O)(=O)c2ccc(Cl)c([N+](=O)[O-])c2)cn1]

4-chloro-N-(4,6-dimethylpyridin-3-yl)-N-isobutyl-3-nitrobenzenesulfonamide

60% sodium hydride (32 mg; 0.80 mmol) is added to 4-chloro-N-(4,6-dimethylpyridin-3-yl)-3-nitrobenzenesulfonamide (248 mg; 0.73 mmol) and 1-iodo-2-methylpropane (125 μl; 1.09 mmol) dissolved in N,N-dimethylformamide (6.6 ml). The reaction medium is stirred for 8 hours at a temperature of 80° C., hydrolyzed and extracted with ethyl acetate. The organic phases are combined, washed with brine and dried (MgSO₄). The solvents are evaporated off.

The crude product is purified by chromatography on silica gel (heptane/ethyl acetate from 20 to 60%). The 4-chloro-N-(4,6-dimethylpyridin-3-yl)-N-isobutyl-3-nitrobenzenesulfonamide (140 mg; 48%) is obtained in the form of a white solid with a compliant $^1$H NMR.

MS: [M+H]=398

3. Synthesis of Intermediate 21.3

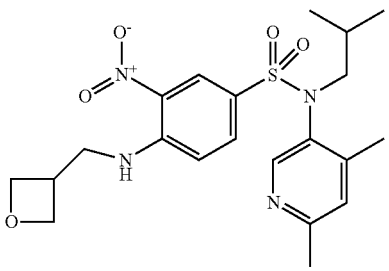 [SMILES: Cc1cc(C)c(N(CC(C)C)S(=O)(=O)c2ccc(NCC3COC3)c([N+](=O)[O-])c2)cn1]

N-(4,6-dimethylpyridin-3-yl)-N-isobutyl-3-nitro-4-[(oxetan-3-ylmethyl)amino]benzenesulfonamide Potassium carbonate (72 mg; 0.52 mmol) and then oxetan-3-ylmethylamine (31.96 mg; 0.37 mmol) are added to a solution of 4-chloro-N-(4,6-dimethylpyridin-3-yl)-N-isobutyl-3-nitrobenzenesulfonamide (139 mg; 0.35 mmol) in N,N-dimethylformamide (1.4 ml). The reaction medium is stirred for 16 hours at room temperature, hydrolyzed and extracted with ethyl acetate. The organic phase is washed with brine, dried over anhydrous magnesium sulfate, filtered and concentrated. The crude product is purified by chromatography on silica gel (heptane/ethyl acetate, from 20 to 60% and then to 50% of ethyl acetate). The N-(4,6-dimethylpyridin-3-yl)-N-isobutyl-3-nitro-4-[(oxetan-3-ylmethyl)amino]benzenesulfonamide (123 mg; 78%) is obtained in the form of a yellow solid with a compliant $^1$H NMR.

MS: [M+H]=449

4. Synthesis of Intermediate 21.4

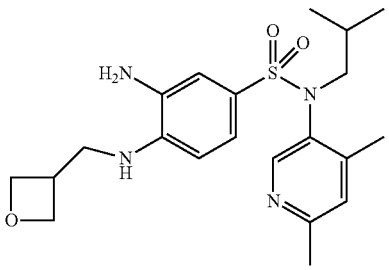 [SMILES: Cc1cc(C)c(N(CC(C)C)S(=O)(=O)c2ccc(NCC3COC3)c(N)c2)cn1]

3-amino-N-(4,6-dimethylpyridin-3-yl)-N-isobutyl-4-[(oxetan-3-ylmethyl)amino]benzenesulfonamide N-(4,6-Dimethylpyridin-3-yl)-N-isobutyl-3-nitro-4-[(oxetan-3-ylmethyl)amino]benzenesulfonamide (120 mg; 0.27 mmol) is dissolved in tetrahydrofuran (1.2 ml). The medium is degassed and 10% palladium on activated charcoal, stabilized with 50% of water (57 mg; 0.03 mmol) is then added. The reaction medium is placed under an atmosphere of dihydrogen and stirred for 4 hours at room temperature. The reaction medium is filtered through Celite. The filtrate is concentrated under vacuum.

The 3-amino-N-(4,6-dimethylpyridin-3-yl)-N-isobutyl-4-[(oxetan-3-ylmethyl)amino]benzenesulfonamide (112 mg; 100%) is obtained in the form of a gray film with a compliant $^1$H NMR.

MS: [M+H]=419

5. Synthesis of 1-oxetan-3-ylmethyl-2-oxo-2,3-dihydro-1H-benzimidazole-5-sulfonic acid (4,6-dimethylpyridin-3-yl)isobutylamide N,N'-Carbonyldiimidazole (128 mg; 0.79 mmol) is added to a solution of 3-amino-N-(4,6-dimethylpyridin-3-yl)-N-isobutyl-4-[(oxetan-3-ylmethyl)amino]benzenesulfonamide (110 mg; 0.26 mmol) in tetrahydrofuran (1.1 ml). The reaction medium is stirred for 17 hours at a temperature of 60° C., hydrolyzed with water and extracted with ethyl acetate.

The organic phase is separated out by settling, washed with water, dried (MgSO$_4$), filtered and concentrated.

The crude product is purified by preparative HPLC (C18 column, eluent: acetonitrile in water/0.1% of formic acid). The 1-oxetan-3-ylmethyl-2-oxo-2,3-dihydro-1H-benzimidazole-5-sulfonic acid (4,6-dimethylpyridin-3-yl)isobutylamide (73 mg; 61%) is obtained in the form of a white solid.

$^1$H NMR (DMSO-d6) δ: 0.77 (d, J=6.7 Hz, 3H), 0.93 (d, J=6.5 Hz, 3H), 1.40 (t, J=7.1 Hz, 1H), 2.22 (s, 3H), 2.41 (s, 3H), 3.18 (dd, J=13.1, 5.0 Hz, 1H), 3.31-3.46 (m, 1H), 4.16 (d, J=7.1 Hz, 2H), 4.41 (t, J=6.1 Hz, 2H), 4.63 (dd, J=7.8, 6.1 Hz, 2H), 7.09 (d, J=1.7 Hz, 1H), 7.20 (s, 1H), 7.30 (dd, J=8.3, 1.7 Hz, 1H), 7.41 (d, J=8.3 Hz, 1H), 7.69 (s, 1H), 11.27 (s, 1H)

MS: [M−H]=445

Example 22: Synthesis of 2-oxo-1-pyridazin-4-ylmethyl-2,3-dihydro-1H-benzimidazole-5-sulfonic acid isopropyl(4-methoxy-2-methylphenyl)amide

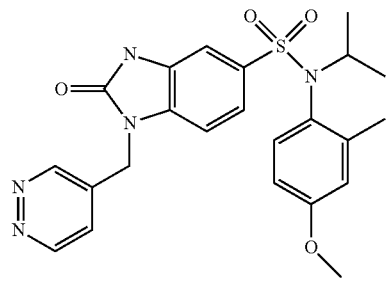 [SMILES: COc1ccc(N(C(C)C)S(=O)(=O)c2ccc3c(c2)[nH]c(=O)n3Cc2ccnnc2)c(C)c1]

1. Synthesis of Intermediate 22.1

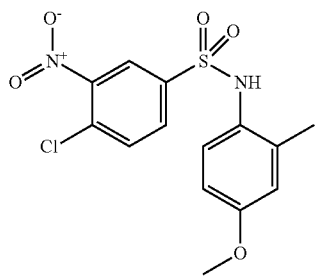 [SMILES: COc1ccc(NS(=O)(=O)c2ccc(Cl)c([N+](=O)[O-])c2)c(C)c1]

4-chloro-N-(4-methoxy-2-methylphenyl)-3-nitrobenzenesulfonamide

4-Chloro-3-nitrobenzenesulfonyl chloride (300 mg; 1.15 mmol) is added to a mixture of 4-methoxy-2-methylaniline (157.5 mg; 1.15 mmol) and pyridine (1.50 ml; 18.6 mmol). The reaction medium is stirred for 3 hours at a temperature of 45° C., hydrolyzed with water and diluted with ethyl acetate. The organic phase is extracted, washed with water, dried (MgSO$_4$), filtered and concentrated. The crude product is purified by preparative HPLC (C18 column, eluent: acetonitrile in water/0.1% of formic acid).

The 4-chloro-N-(4-methoxy-2-methylphenyl)-3-nitrobenzenesulfonamide (264 mg; 64%) is obtained in the form of a purple solid with a compliant $^1$H NMR.

MS: [M−H]=355

2. Synthesis of Intermediate 22.2

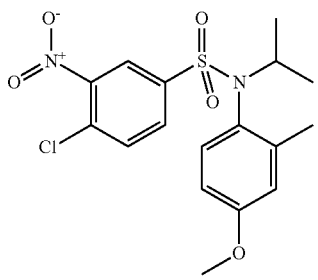 [SMILES: COc1ccc(N(C(C)C)S(=O)(=O)c2ccc(Cl)c([N+](=O)[O-])c2)c(C)c1]

4-chloro-N-isopropyl-N-(4-methoxy-2-methylphenyl)-3-nitrobenzenesulfonamide

60% sodium hydride (26 mg; 0.65 mmol) is added to 4-chloro-N-(4-methoxy-2-methylphenyl)-3-nitrobenzenesulfonamide (210 mg; 0.59 mmol) and 2-iodopropane (90 µl: 0.88 mmol) dissolved in N,N-dimethylformamide (5.5 ml), at a temperature of 0° C. The reaction medium is stirred for 18 hours at a temperature of 30° C., hydrolyzed and extracted with ethyl acetate. The organic phases are combined, washed with saturated sodium chloride solution and dried (MgSO$_4$). The solvents are evaporated off.

The crude product is purified by chromatography on silica gel (heptane/ethyl acetate, from 5 to 20% of ethyl acetate). The 4-chloro-N-isopropyl-N-(4-methoxy-2-methylphenyl)-3-nitrobenzenesulfonamide (183 mg; 78%) is obtained in the form of a colorless paste which crystallizes to a white solid, with a compliant $^1$H NMR.

MS: [M+H]=399

3. Synthesis of Intermediate 22.3

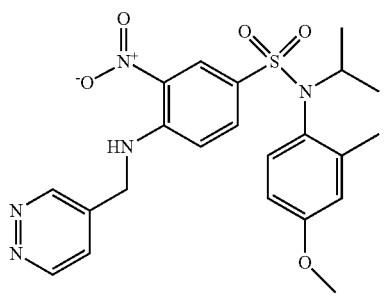

N-Isopropyl-N-(4-methoxy-2-methylphenyl)-3-nitro-4-[(pyridazin-4-ylmethyl)amino]benzenesulfonamide N,N-Diisopropylethylamine (300 µl; 1.75 mmol) is added to a solution of 4-chloro-N-isopropyl-N-(4-methoxy-2-methylphenyl)-3-nitrobenzenesulfonamide (167 mg; 0.42 mmol) in N,N-dimethylformamide (1.7 ml), followed by addition of pyridazin-4-ylmethanammonium dihydrochloride (80 mg; 0.44 mmol).

The reaction medium is stirred for 30 hours at room temperature, hydrolyzed with water, and ethyl acetate and brine are then added. The organic phase is extracted, washed with water and with brine, dried (MgSO$_4$), filtered and concentrated.

The crude product is chromatographed on silica gel, eluting with heptane/ethyl acetate, from 30 to 100% of ethyl acetate. The N-isopropyl-N-(4-methoxy-2-methylphenyl)-3-nitro-4-[(pyridazin-4-ylmethyl)amino]benzenesulfonamide (100 mg; 51%) is obtained in the form of a yellow film with a compliant $^1$H NMR.

MS: [M+H]=472

4. Synthesis of Intermediate 22.4

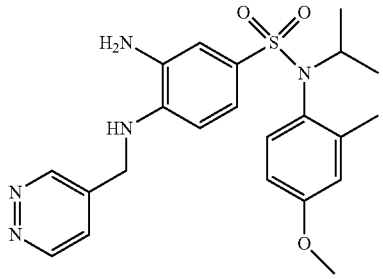 [SMILES: COc1ccc(N(C(C)C)S(=O)(=O)c2ccc(NCc3ccnnc3)c(N)c2)c(C)c1]

3-amino-N-(4,6-dimethylpyridin-3-yl)-N-isobutyl-4-[(oxetan-3-ylmethyl)amino]benzenesulfonamide With a procedure similar to that described for intermediate 21.4, 3-amino-N-isopropyl-N-(4-methoxy-2-methylphenyl)-4-[(pyridazin-4-ylmethyl)amino]benzenesulfonamide (94 mg; 100%) is obtained in the form of a dark oil with a compliant $^1$H NMR.

MS: [M+H]=442

5. Synthesis of 2-oxo-1-pyridazin-4-ylmethyl-2,3-dihydro-1H-benzimidazole-5-sulfonic acid isopropyl (4-methoxy-2-methylphenyl)amide With a procedure similar to that described in example 21, 2-oxo-1-pyridazin-4-ylmethyl-2,3-dihydro-1H-benzimidazole-5-sulfonic acid isopropyl(4-methoxy-2-methylphenyl)amide (23 mg; 23%) is obtained in the form of a white solid.

$^1$H NMR (DMSO-d6) δ: 0.85 (d, J=6.7 Hz, 3H), 0.97 (d, J=6.6 Hz, 3H), 2.24 (s, 3H), 3.76 (s, 3H), 4.32-4.54 (m, 1H), 5.21 (s, 2H), 6.47-6.80 (m, 2H), 6.91 (d, J=2.9 Hz, 1H), 7.16-7.57 (m, 4H), 9.04-9.35 (m, 2H), 11.44 (s, 1H)

MS: [M−H]=468

The invention claimed is:

1. A compound of formula (I), or the pharmaceutically acceptable addition salts thereof hydrates thereof and/or solvates thereof:

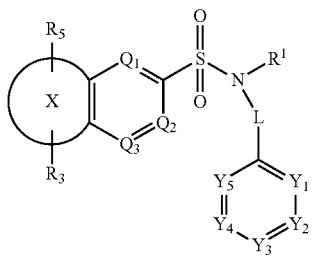

in which formula (I):
L represents a single bond or a methylene group $CH_2$,
X represents the following cyclic radical:

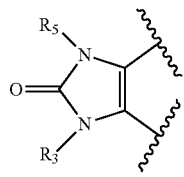

one or two of the elements $Y_1$, $Y_2$, $Y_3$, $Y_4$, and $Y_5$ represent(s) a nitrogen atom and the other elements correspond to a group $CR^2$, or each of the elements $Y_1$, $Y_2$, $Y_3$, $Y_4$, and $Y_5$ corresponds to a group $—CR^2$, one or two of the elements $Q_1$, $Q_2$, and $Q_3$ represent(s) a nitrogen atom and the other element(s) correspond(s) to a group $—CR^{2a}$, or each of the elements $Q_1$, $Q_2$, and $Q_3$ corresponds to a group $—CR^{2a}$, $R^1$ represents a linear or branched $C_3$-$C_5$ alkyl radical, a $C_3$-$C_5$ cycloalkyl radical, a linear or branched $C_2$-$C_5$ alkenyl radical, a $—CH_2—(C_3$-$C_5)$cycloalkyl radical, a $C_4$-$C_5$ heterocycloalkyl radical, or a $—CH_2—(C_4$-$C_6)$ heterocycloalkyl radical; with the proviso that when L is $CH_2$, $R^1$ is a $C_4$-$C_5$ heterocycloalkyl radical or a $—CH_2—(C_4$-$C_6)$heterocycloalkyl radical, $R^2$ represents a hydrogen atom or a halogen atom, a linear or branched $C_1$-$C_5$ alkyl radical, a linear or branched $C_2$-$C_4$ alkenyl radical, a $C_1$-$C_4$ alkoxy radical, a cyano group $—CN$, a radical $—C(\!=\!O)R'^2$ with $R'^2$ denoting a $C_1$-$C_3$ alkoxy radical, or a $—CF_3$ radical; said alkyl, alkenyl and alkoxy radicals optionally being substituted with one or more halogen atoms;

$R^{2a}$ represents a hydrogen atom or a halogen atom, a linear or branched $C_1$-$C_5$ alkyl radical, a linear or branched $C_2$-$C_4$ alkenyl radical, a $C_1$-$C_4$ alkoxy radical, a $—CN$ group, a hydroxyl group $—OH$, a group $—CH(R^{3a})OH$, a carboxylic group $—COOH$, a carbamoyl group $—CONR^{2c}R^{2d}$, an amido group $—NR^{2c}COR^{2d}$, a group $—SO_2R^{2c}$, a group $—SOR^{2c}$, or a group $—S(\!=\!O)(\!=\!NH—R^{2c})$, said alkyl, alkenyl and alkoxy radicals optionally being substituted with one or more halogen atoms, $R^{2c}$ and $R^{2d}$, which are identical or different, represent a hydrogen atom or a linear or branched $C_1$-$C_5$ alkyl radical;

$R^{3a}$ represents a hydrogen atom or a linear or branched $C_1$-$C_5$ alkyl radical;

$R_3$ represents a hydrogen atom or a group $(CHR^6)_n—(Z)_o—(CHR'^6)_p—R^7$, n, o and p, which are identical or different, represent zero or a natural integer ranging from 1 to 3, Z represents a divalent group selected from the group consisting of a methylene group $—CH_2—$, an amino group $—NH—$ and an oxygen atom $—O—$, $R^6$ and $R'^6$, which are identical or different, represent a hydrogen atom, a methyl group $—CH_3$, a group $—OH$, a hydroxymethyl group, or a carboxylic function $—COOH$, $R^7$ represents:
a hydrogen or halogen atom,
a group $COOR'^7$ with $R'^7$ denoting $(C_1)$alkyl$(C_6)$heterocycle,
a non-cationic heterocycloalkyl radical optionally substituted with one or more halogen atoms, one or more linear or branched $C_1$-$C_3$ alkyl groups, one or more $—OH$ groups, one or more carbonyl functions, one or more linear or branched $C_1$-$C_4$ hydroxyalkyl groups, one or more amino groups, one or more groups $—C(\!=\!O)R_{7a}$, one or more groups $S(\!=\!O)_2R_{7a}$; $R_{7a}$ representing a linear or branched $C_1$-$C_3$ alkyl radical, a linear or branched $C_1$-$C_3$ alkoxy radical, or an amino radical $N(R^{8a})(R^{8b})$, a non-cationic $C_3$-$C_6$ cycloalkyl radical optionally substituted with one or more methyl radicals, one or more halogen atoms, a cyano group $—CN$ or one or more groups $—COR^{13}$; $R^{13}$ denoting a linear or branched $C_1$-$C_3$ alkoxy radical, or a hydroxyl group, or an aromatic or heteroaromatic, non-cationic radical optionally substituted with one or more halogen atoms, one or more linear or branched $C_1$-$C_3$ alkyl groups optionally substituted with one or more halogen atoms, one or more $C_1$-$C_3$ alkoxy groups, one or more amino groups $—NR^{11}R^{12}$, one or more groups $—COR^{11}$, one or more groups $—COOR^{11}$, one or more amido groups $—CONR^{11}R^{12}$, one or more groups $—SOR^{11}$, one or more groups $SO_2R^{11}$, one or more groups $—NHCOR^{11}$ one or more groups $—NHCOOR^{11}$, one or more groups $—SO_2NR^{11}R^{12}$ or one or more $—CN$ groups; $R^{11}$ and $R^{12}$, which are identical or different, representing a hydrogen atom, a hydroxyl radical $—OH$, a linear or branched $C_1$-$C_3$ alkyl radical optionally substituted with one or more halogen atoms, $R_5$ represents a hydrogen atom or a halogen atom, a linear or branched $C_1$-$C_3$ alkyl radical optionally substituted with one or more halogen atoms; an amino radical $—NH_2$, a radical $CH_2R'^{7a}$ with $R'^{7a}$ denoting a methoxy radical, a hydroxyl group $—OH$, a $—CH_2COOH$ group, a group $—CH(R^{5b})OH$, a carboxylic group $—COOH$, a $—CN$ group, or a thioxo function, $R^{5b}$ represents a hydrogen atom; a linear or branched $C_1$-$C_3$ alkyl radical optionally substituted with one or more carboxylic functions; a cyclopropyl radical, $R^{8a}$ and $R^{8b}$, which are identical or different, denote a hydrogen atom, a linear or branched $C_1$-$C_3$ alkyl radical or a cyclopropyl radical.

2. The compound of formula (I) as defined by claim 1, wherein $R^7$ represents a heterocyclic radical selected from the group consisting of:

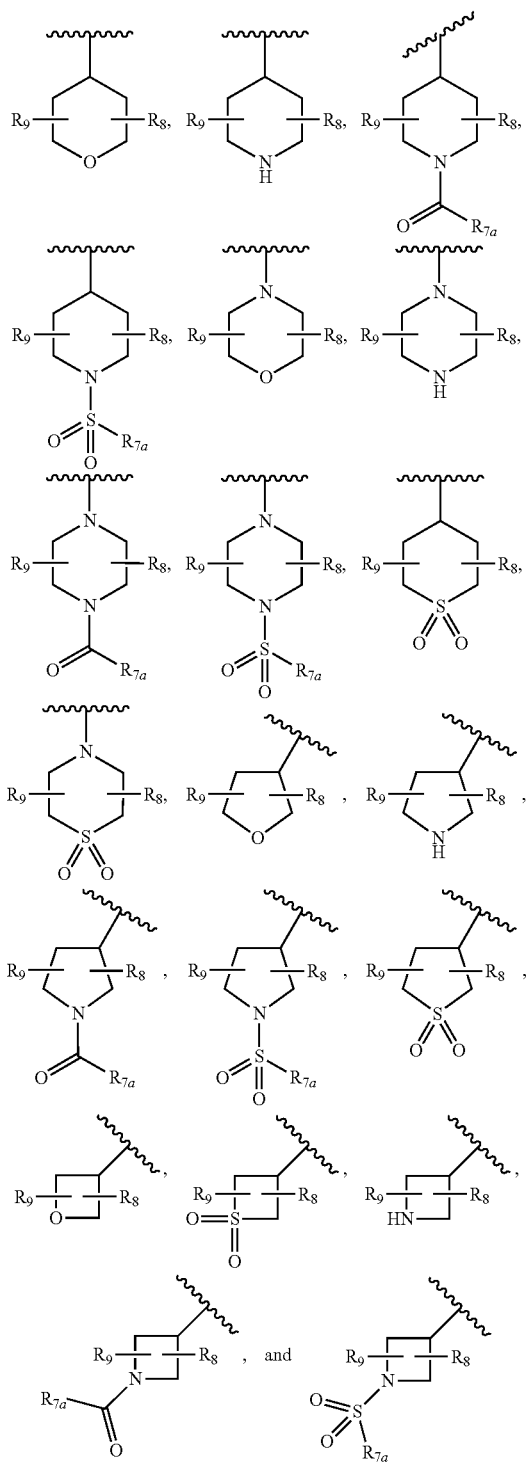

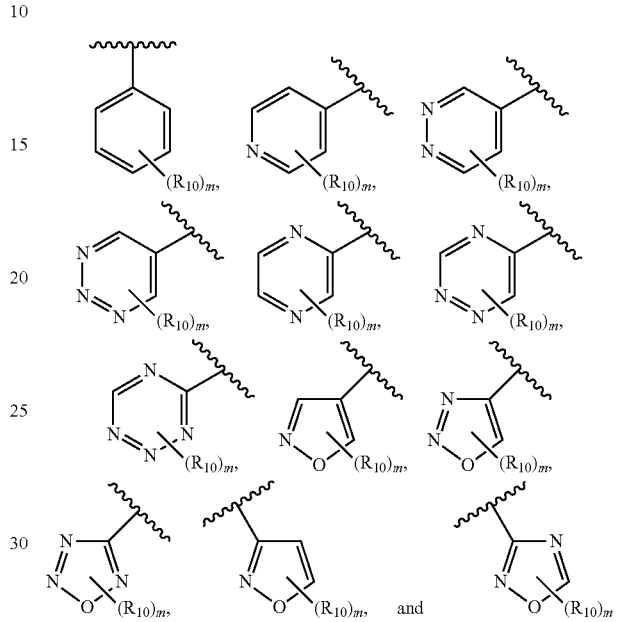

in which:
R$_{7a}$ represents a linear or branched C$_1$-C$_3$ alkyl radical, a linear or branched C$_1$-C$_3$ alkoxy radical or an amino radical N(R$^{8a}$)(R$^{8b}$), R$^{8a}$ and R$^{8b}$, which are identical or different, denote a hydrogen atom, a linear or branched C$_1$-C$_3$ alkyl radical or a cyclopropyl radical, R$_8$ and R$_9$, which are identical or different, represent a hydrogen atom, a linear or branched C$_1$-C$_3$ alkyl radical, a hydroxyl group —OH, a carbonyl function =O, a (C$_1$)hydroxyalkyl radical (—CH$_2$OH), or an amino group NH$_2$, or R$_8$ and R$_9$ can form, together with the carbon atoms to which they are attached, a 5- to 7-membered carbocyclic ring.

3. The compound of formula (I) as defined by claim 1, wherein R$^7$ represents an aromatic or heteroaromatic radical selected from the group consisting of:

in which:
R$_{10}$ represents a hydrogen atom or a halogen atom, a linear or branched C$_1$-C$_3$ alkyl group optionally substituted with one or more halogen atoms; a C$_1$-C$_3$ alkoxy group, an amino group —NR$^{11}$R$^{12}$, a group —COR$^{11}$, a group —COOR$^{11}$, an amido group —CONR$^{11}$R$^{12}$, a group —SOR$^{11}$, a group —SO$_2$R$^{11}$, a group —NHCOR11 a group —NHCOOR$^{11}$, a group —SO$_2$NR$^{11}$R$^{12}$ or a —CN group; R$^{11}$ and R$^{12}$, which are identical or different, representing a hydrogen atom or a linear branched C$_1$-C$_3$ alkyl radical optionally substituted with one or more halogen atoms and m denotes zero or a natural integer ranging from 1 to 3.

4. The compound of formula (I) as defined by claim 1, wherein the compound has the structure of formula (IV), or pharmaceutically acceptable addition salts thereof, hydrates thereof and/or solvates thereof:

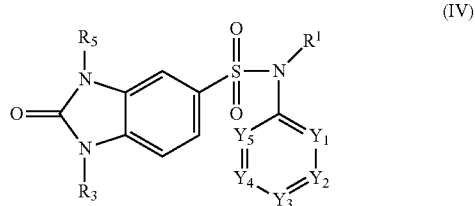

(IV)

in which formula (IV) R$^1$, R$_3$, R$_5$ and Y$_1$ to Y$_5$ have the same meanings as in formula (I).

5. The compound of formula (I) as defined by claim 1, wherein R$^1$ represents a linear or branched C$_3$-C$_5$ alkyl radical or a C$_3$-C$_5$ cycloalkyl radical.

6. The compound of formula (I) as defined by claim 1, wherein $R_5$ represents a hydrogen atom.

7. The compound of formula (I) as defined by claim 1, wherein $R_3$ represents a group $(CHR^6)_n—(Z)_o—(CHR'^6)_p—R^7$ with the indices n, p, o, $R^6$, $R'^6$ and $R^7$ having the same meanings as defined in claim 1.

8. The compound of formula (I) as defined by claim 1, wherein the compound is selected from the group consisting of:

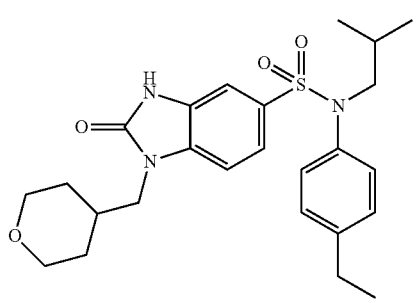

Compound 2

2-oxo-1-(tetrahydropyran-4-ylmethyl)-2,3-dihyro-1H-benzimidazole-5-sulfonic acid (4-ethylphenyl)isobutylamide,

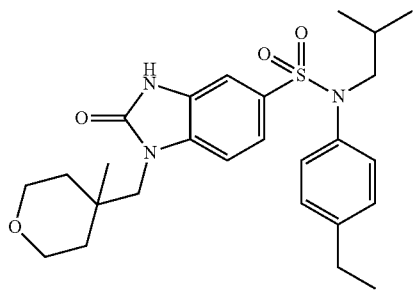

Compound 4

1-(4-methyltetrahydropyran-4-ylmethyl)-2-oxo-2,3-dihydro-1H-benzimidazole-5-sulfonic acid (4-ethylphenyl)isobutylamide,

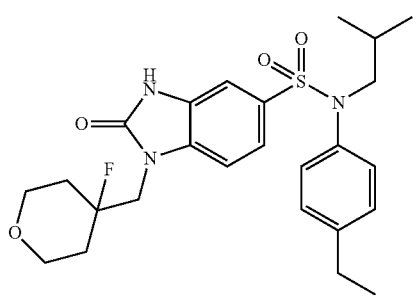

Compound 5

1-(4-fluorotetrahydropyran-4-ylmethyl)-2-oxo-2,3-dihydro-1H-benzimidazole-5-sulfonic acid (4-ethylphenyl)isobutylamide, -continued

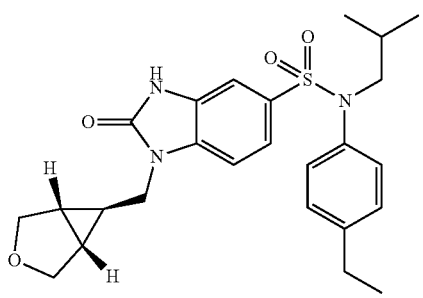

Compound 6

1-[(1R,5S,6S)-1-(3-oxabicyclo[3.1.0]hex-6-yl)methyl]-2-oxo-2,3-dihydro-1H-benzimidazole-5-sulfonic acid (4-ethylphenyl)isobutylamide,

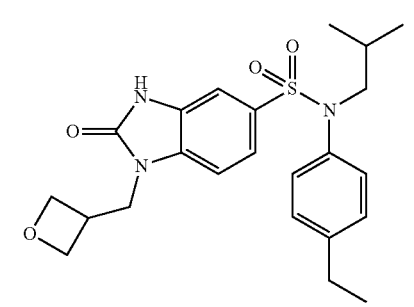

Compound 7

1-oxetan-3-ylmethyl-2-oxo-2,3-dihydro-1H-benzimidazole-5-sulfonic acid (4-ethylphenyl)isobutylamide,

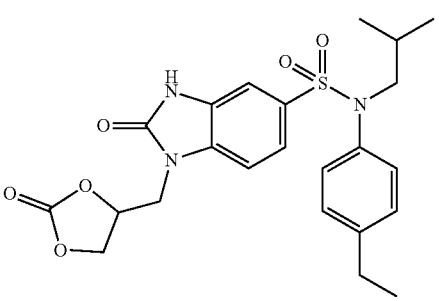

Compound 8

2-oxo-1-(2-oxo[1,3]dioxolan-4-ylmethyl)-2,3-dihydro-1H-benzimidazole-5-sulfonic acid (4-ethylphenyl)isobutylamide,

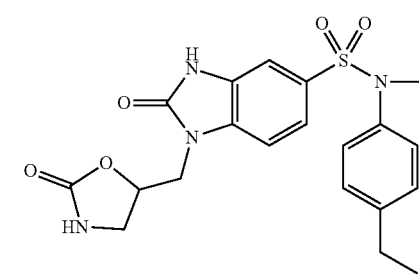

Compound 9

2-oxo-1-(2-oxooxazolidin-5-ylmethyl)-2,3-dihydro-1H-benzimidazole-5-sulfonic acid (4-ethylphenyl)isobutylamide, Compound 10

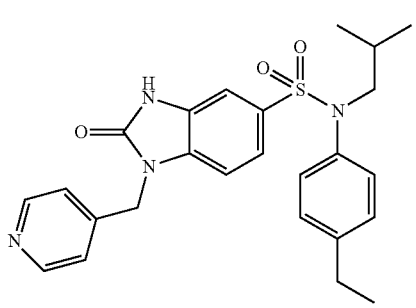

2-oxo-1-pyridin-4-ylmethyl)-2,3-dihydro-1H-benzimidazole-5-sulfonic acid (4-ethylphenyl)isobutylamide, Compound 11

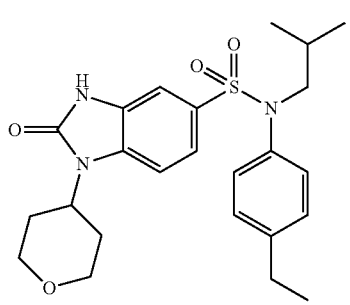

2-oxo-1-(tetrahydropyran-4-yl)-2,3-dihydro-1H-benzimidazole-5-sulfonic acid (4-ethylphenyl)isobutylamide, Compound 13

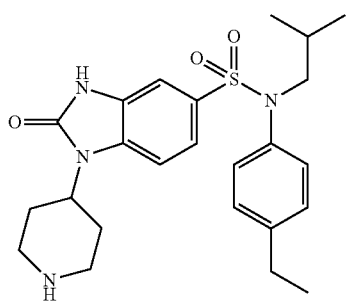

2-oxo-1-piperidin-4-yl-2,3-dihydro-1H-benzimidazole-5-sulfonic acid (4-ethylphenyl)isobutylamide, Compound 14

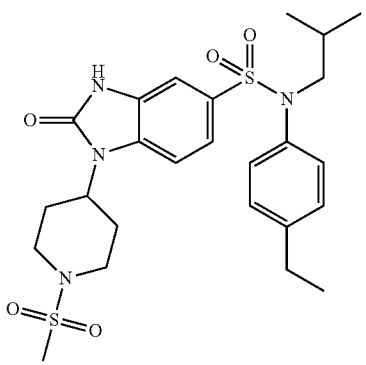

1(1-methanesulfonylpiperidin-4-yl)-2-oxo-2,3,dihydro-1H-benzimidazole-5-sulfonic acid (4-ethylphenyl)isobutylamide, Compound 15

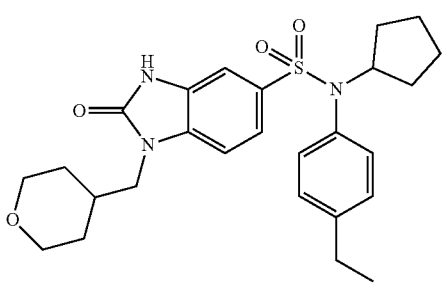

2-oxo-1-(tetrahydropyran-4-ylmethyl)-2,3-dihydro-1H-benzimidazole-5-sulfonic acid (4-ethylphenyl)cyclopentylamide, Compound 16

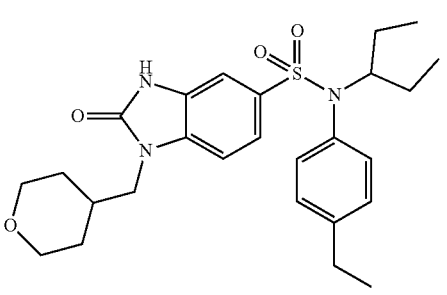

2-oxo-1-(tetrahydropyran-4-ylmethyl)-2,3-dihydro-1H-benzimidazole-5-sulfonic acid (4-ethylphenyl)(1-ethylpropyl)amide, Compound 17

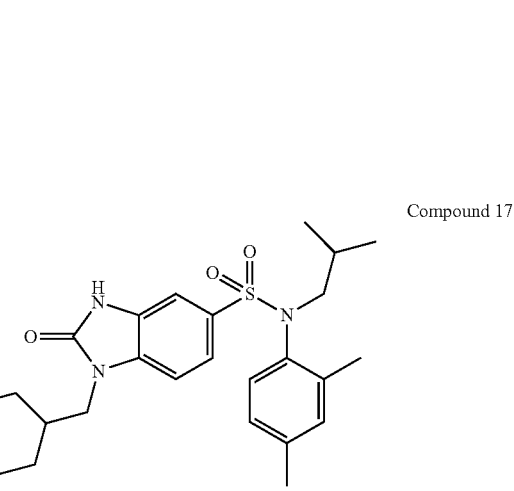

2-oxo-1-(tetrahydropyran-4-ylmethyl)-2,3-dihydro-1H-benzimidazole-5-sulfonic acid (2,4-dimethylphenyl)isobutylamide, -continued Compound 18

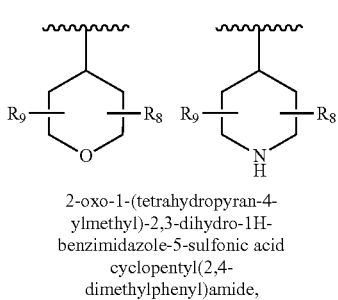

2-oxo-1-(tetrahydropyran-4-
ylmethyl)-2,3-dihydro-1H-
benzimidazole-5-sulfonic acid
cyclopentyl(2,4-
dimethylphenyl)amide, Compound 19

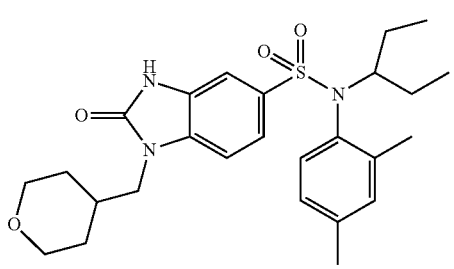

2-oxo-1-(tetrahydropyran-4-
ylmethyl)-2,3-dihydro-1H-
benzimidazole-5-sulfonic acid
(2,4-dimethylphenyl)(1-
ethylpropyl)amide, and -continued Compound 22

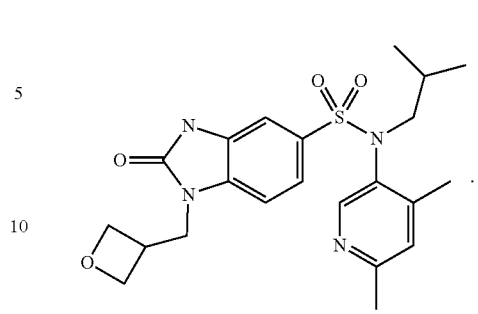

1-oxetan-3-ylmethyl-2-oxo-2,3-
dihydro-1H-benzimidazole-5-
sulfonic acid (4,6-dimethylpyridin-
3-yl)isobutylamide 9. A medicament comprising an effective amount of the compound defined by claim 1.

10. A method of treating acne, the method comprising administering an effective amount of the compound defined by claim 1 to an individual subject in need thereof.

11. A method of treating psoriasis, the method comprising administering an effective amount of the compound defined by claim 1 to an individual subject in need thereof.

12. A pharmaceutical composition comprising one or more compounds as defined by claim 1.

13. The pharmaceutical composition as defined by claim 12, wherein the composition is formulated for treating acne, atopic dermatitis and/or psoriasis.

* * * * *